(12) United States Patent
Dickinson et al.

(10) Patent No.: US 7,572,280 B2
(45) Date of Patent: Aug. 11, 2009

(54) MULTI-AXIAL ANCHOR ASSEMBLIES FOR SPINAL IMPLANTS AND METHODS

(75) Inventors: Charles A. Dickinson, Millington, TN (US); Harold S. Taylor, Memphis, TN (US); Terrance Strohkirch, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 286 days.

(21) Appl. No.: 11/117,919

(22) Filed: Apr. 29, 2005

(65) Prior Publication Data

US 2006/0084989 A1    Apr. 20, 2006

Related U.S. Application Data

(63) Continuation-in-part of application No. 10/958,977, filed on Oct. 5, 2004.

(51) Int. Cl.
*A61B 17/70* (2006.01)
(52) U.S. Cl. ..................................... 606/266
(58) Field of Classification Search .............. 606/54, 606/60, 61, 72, 73
See application file for complete search history.

(56) References Cited

U.S. PATENT DOCUMENTS

| | | | |
|---|---|---|---|
| 4,569,338 A | 2/1986 | Edwards |
| 4,827,918 A | 5/1989 | Olerud |
| 5,047,029 A | 9/1991 | Aebi et al. |
| 5,053,034 A | 10/1991 | Olerud |
| 5,176,680 A | 1/1993 | Vignaud et al. |
| 5,234,431 A | 8/1993 | Keller |
| 5,254,118 A | 10/1993 | Mirkovic |
| 5,474,555 A | 12/1995 | Puno et al. |
| 5,527,314 A | 6/1996 | Brumfield et al. |
| 5,527,315 A * | 6/1996 | Jeanson et al. ............... 606/61 |
| 5,534,002 A | 7/1996 | Brumfield et al. |
| 5,540,690 A | 7/1996 | Miller et al. |
| 5,545,166 A | 8/1996 | Howland |
| 5,562,662 A | 10/1996 | Brumfield |
| 5,569,247 A | 10/1996 | Morrison |
| 5,591,166 A | 1/1997 | Bernhardt et al. |
| 5,628,740 A | 5/1997 | Mullane |
| 5,643,263 A | 7/1997 | Simonson |
| 5,643,265 A | 7/1997 | Errico et al. |

(Continued)

FOREIGN PATENT DOCUMENTS

EP    947174 A2 * 10/1999

OTHER PUBLICATIONS

TiMX Comprehensive Low Back System, DePuy Acromed, © 1999.

(Continued)

*Primary Examiner*—Eduardo C Robert
*Assistant Examiner*—Nicholas Woodall

(57) ABSTRACT

Systems and methods are provided that include a plate member engageable to the spinal column with an anchor assembly. The anchor assembly includes a coupling member having a post extending through at least one opening of the plate member and an anchor member pivotally captured in a receiver member of the coupling member below a lower surface of the plate member. A locking member secures the plate member to the coupling member. A crown in the receiver member of the coupling member is engaged by the plate member to secure the anchor member in position relative to the coupling member.

22 Claims, 21 Drawing Sheets

U.S. PATENT DOCUMENTS

| | | | |
|---|---|---|---|
| 5,725,528 A | 3/1998 | Errico et al. | |
| 5,735,851 A | 4/1998 | Errico et al. | |
| 5,800,435 A | 9/1998 | Errico et al. | |
| 5,885,285 A | 3/1999 | Simonson | |
| 5,904,683 A | 5/1999 | Pohndorf et al. | |
| 5,938,663 A | 8/1999 | Petreto | |
| 5,947,967 A | 9/1999 | Barker | |
| 6,010,504 A | 1/2000 | Rogozinski | |
| 6,050,997 A | 4/2000 | Mullane | |
| 6,132,432 A | 10/2000 | Richelsoph | |
| 6,183,473 B1 | 2/2001 | Ashman | |
| 6,187,005 B1 | 2/2001 | Brace et al. | |
| 6,210,413 B1 | 4/2001 | Justis | |
| 6,248,107 B1 | 6/2001 | Foley | |
| 6,267,765 B1 | 7/2001 | Taylor et al. | |
| 6,280,442 B1 | 8/2001 | Barker et al. | |
| 6,302,888 B1 * | 10/2001 | Mellinger et al. | 606/270 |
| 6,315,779 B1 | 11/2001 | Morrison et al. | |
| 6,352,537 B1 | 3/2002 | Strnad | |
| 6,355,038 B1 | 3/2002 | Pisharodi | |
| 6,478,798 B1 | 11/2002 | Howland | |
| 6,520,962 B1 | 2/2003 | Taylor et al. | |
| 6,524,315 B1 | 2/2003 | Selvitelli et al. | |
| 6,547,790 B2 | 4/2003 | Harkey, III et al. | |
| 6,562,038 B1 | 5/2003 | Morrison | |
| 6,626,906 B1 | 9/2003 | Young | |
| 6,685,705 B1 | 2/2004 | Taylor et al. | |
| 6,770,075 B2 | 8/2004 | Howland | |
| 2003/0073996 A1 | 4/2003 | Doubler et al. | |
| 2003/0125741 A1 * | 7/2003 | Biedermann et al. | 606/61 |
| 2004/0116929 A1 * | 6/2004 | Barker et al. | 606/61 |
| 2005/0177154 A1 * | 8/2005 | Moumene et al. | 606/61 |
| 2005/0261687 A1 * | 11/2005 | Garamszegi et al. | 606/61 |
| 2005/0277923 A1 * | 12/2005 | Sweeney | 606/61 |
| 2005/0277928 A1 * | 12/2005 | Boschert | 606/61 |
| 2006/0084980 A1 * | 4/2006 | Melkent et al. | 606/61 |
| 2006/0264933 A1 * | 11/2006 | Baker et al. | 606/61 |
| 2007/0016188 A1 * | 1/2007 | Boehm et al. | 606/60 |

OTHER PUBLICATIONS

Pass® Deformity System, Encore Surgical, © Jan. 2002.
Spine Internal Fixation Device, Encore Surgical, © Jan. 2002.

* cited by examiner

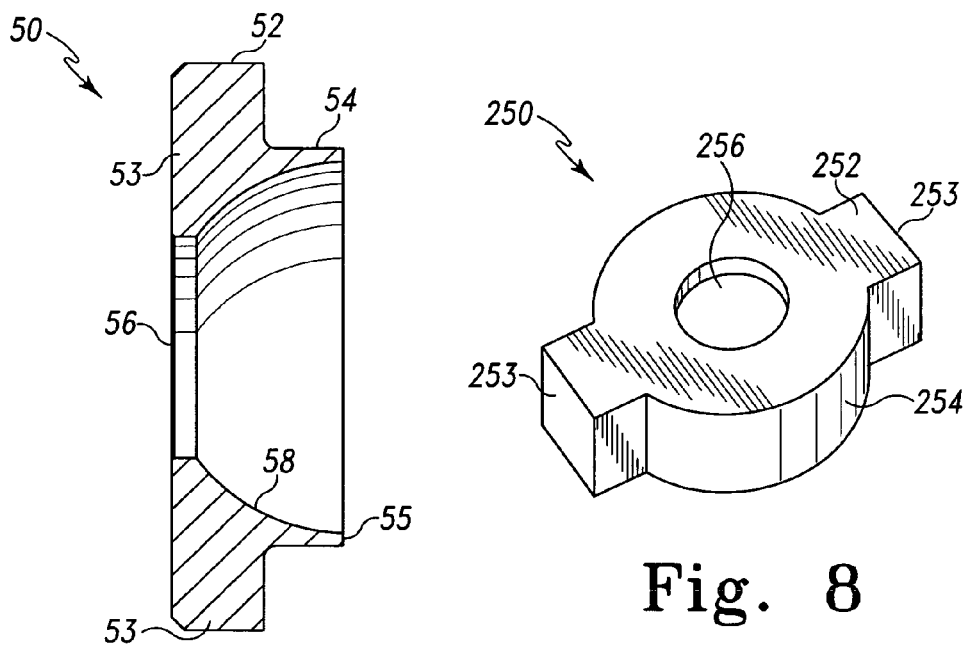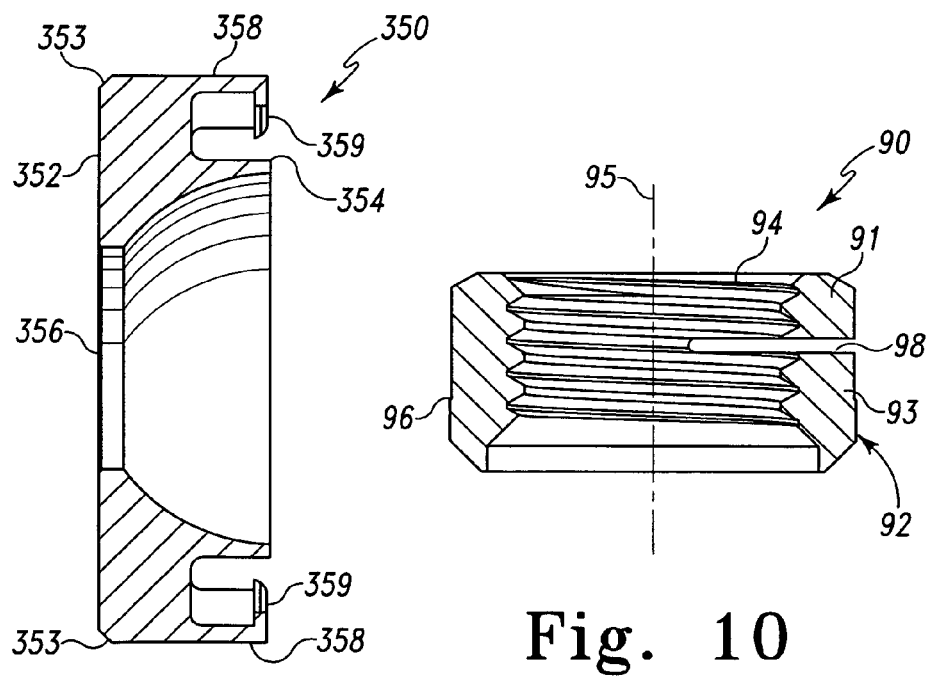

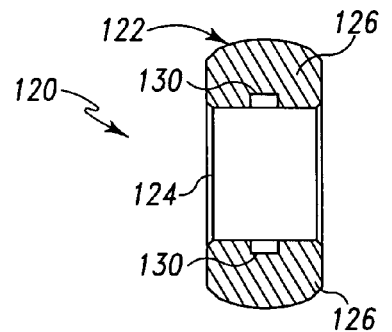
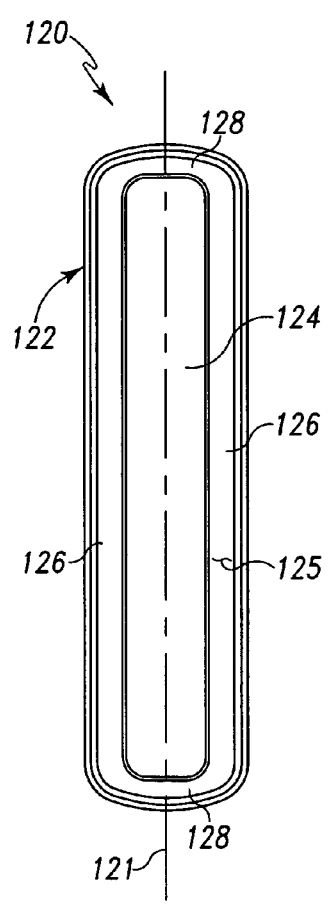
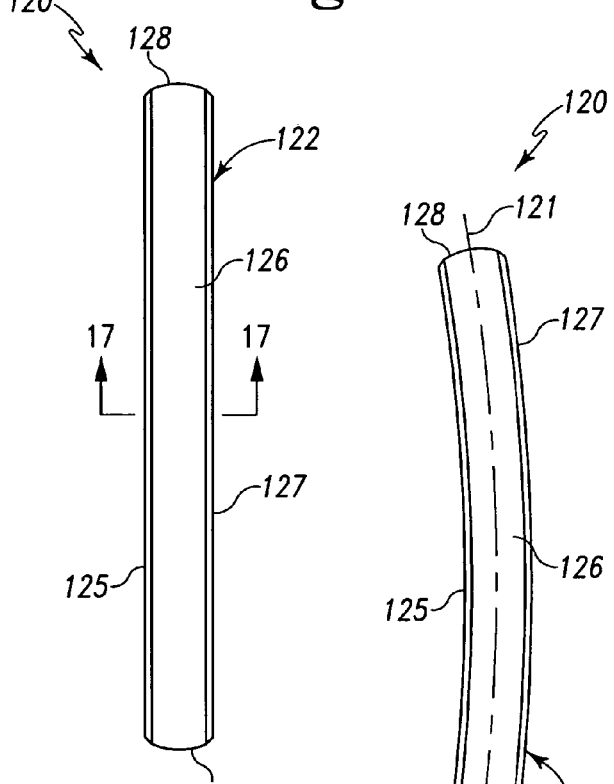
Fig. 17
Fig. 15    Fig. 16    Fig. 18

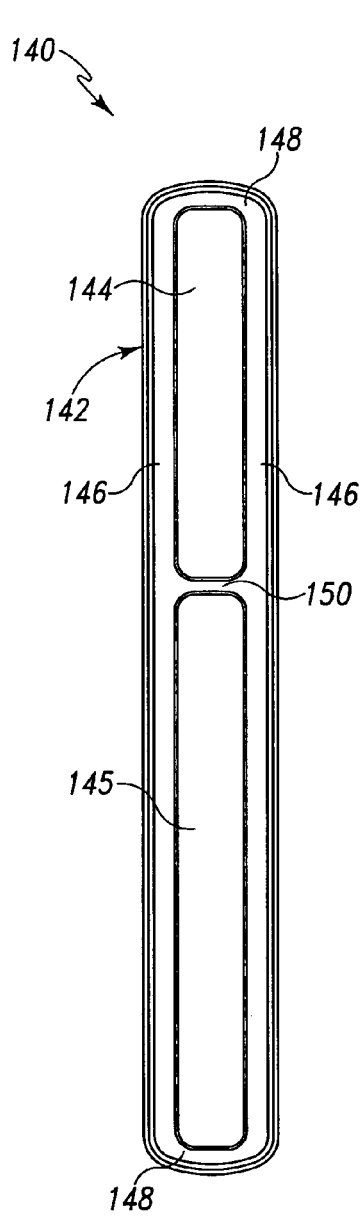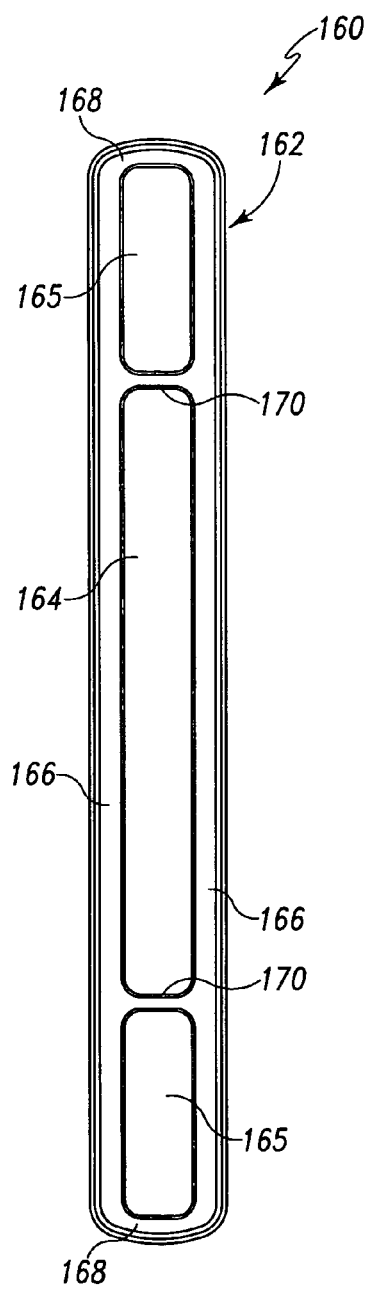
Fig. 19
Fig. 20

MULTI-AXIAL ANCHOR ASSEMBLIES FOR SPINAL IMPLANTS AND METHODS

CROSS-REFERENCE TO RELATED APPLICATION

This application is a continuation-in-part of U.S. patent application Ser. No. 10/958,977, filed on Oct. 5, 2004, which is incorporated herein by reference in its entirety.

BACKGROUND

In the art of orthopedic surgery, and particularly in spinal surgery, it has long been known to affix an elongated member, such as a plate or rod, to bones in order to hold them and support them in a given position. For example, in a procedure to fuse damaged, diseased, malformed, or otherwise abnormal or injured vertebrae, the vertebrae are positioned in a corrected position by a surgeon. An elongated plate is placed adjacent to one or more vertebral bodies and bone anchors, such as screws or bolts, are employed to secure the plate to the vertebral bodies. The anchors and plate are secured to each other to minimize or prevent relative movement. In this way, the vertebral bodies may be held and/or supported in proper alignment for healing.

There remains a need for systems, devices and methods that facilitate positioning and attachment of implants to one or more vertebrae of the spinal column, that provide various attachment modes of implants to one or more vertebrae of the spinal column, and that provide multi-axial capabilities for the anchor assemblies employed in attaching implants to one or more vertebrae of the spinal column.

SUMMARY

The present invention relates to orthopedic implant systems and methods for use in stabilizing bone members in a desired spatial relationship in correcting bone misalignment disorders, to provide stabilization along one or more vertebral levels, or for spinal or other bone fusion. A multi-axial anchor assembly is engageable to an implant, such as a plate member, rod member, or other connectors or implants to secure the implant to a bony structure.

According to one aspect, an anchor assembly is provided that includes an anchor member having a head and a lower portion extending from the head for engagement with a bone member. The anchor assembly further includes a coupling member pivotally coupled to the head of the anchor. The coupling member includes a lower receiver portion defining an interior receptacle for receiving the head and a post extending from the receiver portion away from the head. The post is configured to engage a locking member. The receiver portion defines a number of openings in communication with an exterior of the coupling member. A crown is positioned in the receptacle of the coupling member about the head of the anchor member. The crown includes a number of axially extending seating portions extending through respective ones of the number of openings. The seating portions are positioned in contact with at least one of an implant member or locking member positioned about the post of the coupling member.

According to another aspect, a spinal plating system includes an implant including at least one opening extending therethrough between an upper surface and an opposite lower surface that is positionable along the spinal column. The system further includes an anchor assembly engageable to the implant. The anchor assembly comprises a coupling member having a post positionable through the at least one opening and a receiver portion positionable toward the lower surface of the implant. The receiver portion includes a receptacle, and the post defines a passage extending from a proximal end thereof to the receptacle. The anchor assembly further comprises an anchor member including a head pivotally captured in the receptacle of the receiver portion and a lower portion extending from the head for engaging a bony structure of the spinal column. A locking member is engageable to the mounting portion of the post in contact with one of the upper surface of the implant or the receiver to secure the implant to the spinal column.

According to another aspect, a spinal plating system includes a plate member including at least one opening extending therethrough between an upper surface and an opposite lower surface that is positionable toward the spinal column. The system further includes an anchor assembly engageable to the plate member. The anchor assembly comprises a coupling member having a post positionable through the at least one opening and a receiver portion positionable along the lower surface of the plate member. The post is threadingly engaged with the receiver portion at a proximal end opening of the receiver portion. The receiver portion includes a receptacle, and an anchor member includes a head pivotally captured in the receptacle of the receiver portion. A lower portion of the anchor member extends from the head for engaging a bony structure of the spinal column. A locking member is engageable to the post in contact with the upper surface of the plate member to secure the plate member to the coupling member between the locking member and the receiver portion.

According to another aspect, a spinal surgical method comprises: accessing at least one vertebra of the spinal column through an incision; engaging an anchor member of an anchor assembly to the at least one vertebra through the incision, the anchor assembly including a coupling member pivotally mounted to the anchor member with a post extending proximally from anchor member; pivoting the coupling member relative to the engaged anchor member to orient the post in a desired position; positioning an elongate plate member about a proximal end of the post; advancing the plate member along the post to a location adjacent the anchor member; engaging the plate member against a crown, the crown extending from the anchor in the coupling member and including multiple seat portion located outside the coupling member against which the plate member is positioned to secure the anchor member in the coupling member.

These and other aspects are discussed further below.

BRIEF DESCRIPTION OF THE DRAWINGS

FIG. 7 is a sectional view of a crown comprising a portion of the anchor assembly of FIG. 1.

FIG. 8 is a perspective view of another embodiment crown.

FIG. 9 is a section view of another embodiment crown.

FIG. 10 is a section view of a locking member engageable to the coupling member of the anchor assembly of FIG. 1.

FIG. 15 is a plan view of one embodiment plate member.

FIG. 16 is an elevational view of the plate member of FIG. 15.

FIG. 17 is a sectional view through line 17-17 of FIG. 16.

FIG. 18 is an elevational view of the plate member of FIG. 15 with a curved longitudinal profile.

FIG. 19 is a plan view of another embodiment plate member.

FIG. 20 is a plan view of another embodiment plate member.

DESCRIPTION OF THE ILLUSTRATED EMBODIMENTS

Figure 1:
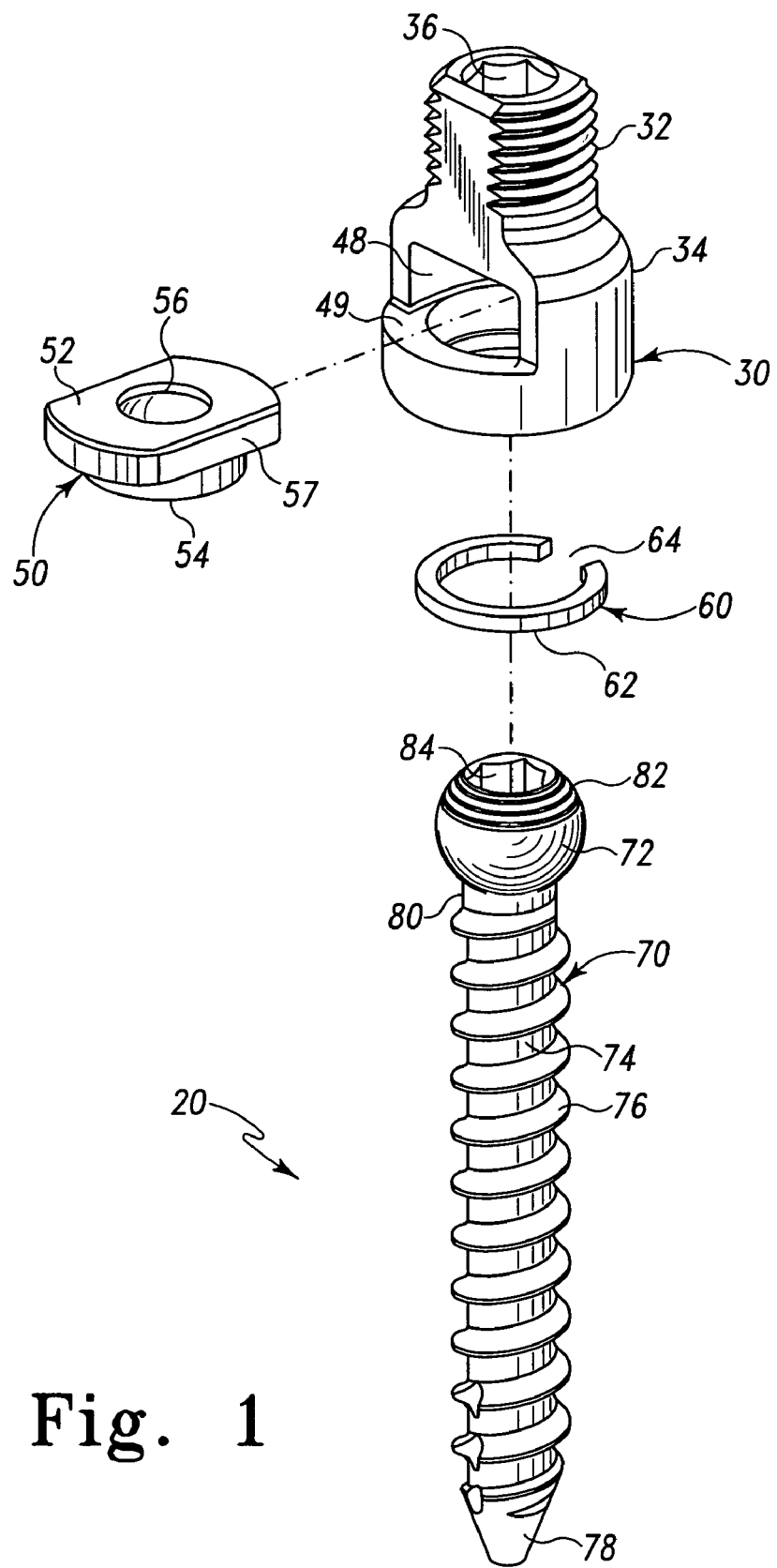
FIG. 1 is an exploded perspective view of a multi-axial anchor assembly.
Figure 2:
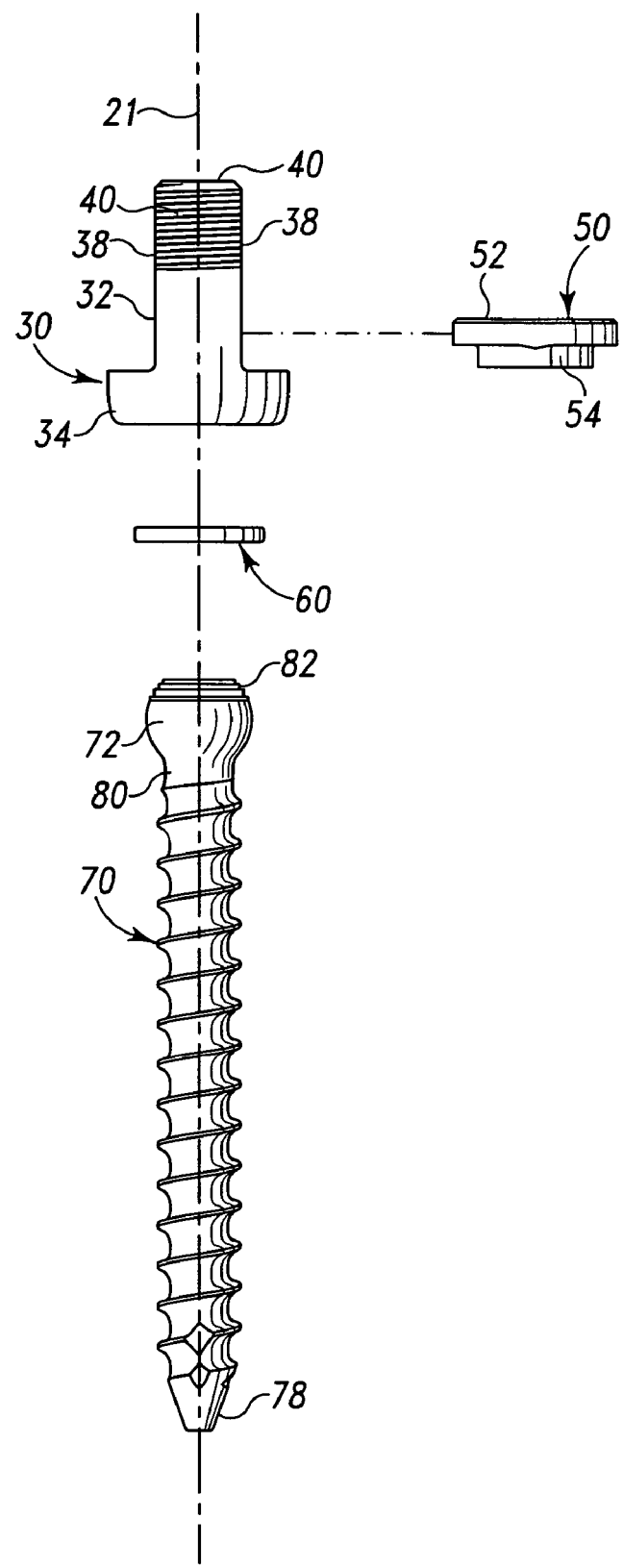
FIG. 2 is an exploded elevational view of the anchor assembly of FIG. 1.

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described processes, systems or devices, and any further applications of the principles of the invention as described herein, are contemplated as would normally occur to one skilled in the art to which the invention relates.

A multi-axial anchor assembly is provided to secure an implant such as a plate member or connector to one or more vertebrae of the spinal column. The anchor assembly includes an anchor member pivotally coupled in a receiver portion of the coupling member. The coupling member includes a post extending proximally from the anchor member for receiving the implant thereabout. The anchor member is pivotal universally about a longitudinal axis of the assembly. In one embodiment, the coupling member can be engaged such that the coupling member is constrained from pivoting in at least one direction relative to the implant while the anchor member is pivotal in the coupling member.

In one form, the coupling member includes a crown in the receiver portion that extends between the anchor and the member positioned about the post. In one embodiment, the crown rigidly engages the anchor member in position relative to the coupling member when the locking member is secured against one of the implant or the crown. In another form, the coupling member includes at least one window and the crown includes a seat portion extending through the at least one window for contact with a lower surface of the implant or the locking member positioned about the post. The locking member can firmly engage one of the seat portion or the implant against the seat portion of the crown when the locking member is finally engaged to the anchor assembly.

In another form, a multi-axial anchor assembly is provided that includes a coupling member for receiving an implant thereabout and an anchor member extending distally of the coupling member. In one application with plate members, before the coupling member is firmly engaged with a locking member it is received in an elongated slot of the plate member such that is non-pivotal transversely to a longitudinal axis of the slot while the anchor member is pivotal in all direction relative to the coupling member. When the locking member is secured to firmly engage the plate member to the coupling member, the coupling member and the anchor member are fixed relative to one another and relative to the plate member.

In another form, a multi-axial anchor assembly is provided that includes a coupling member and an anchor member pivotally mounted in a receiver portion of the coupling member. A post extends proximally from the receiver portion, and receives a locking member. The post includes a mounting portion adjacent the receiver portion to which the locking member is mounted to secure an implant to the coupling member or to engage a crown in the coupling member. An extension portion extends proximally from the mounting portion to facilitate placement of the implant about the post. The extension portion is removable from the mounting portion to minimize intrusion of the anchor assembly into adjacent tissue post-operatively.

Figure 14:
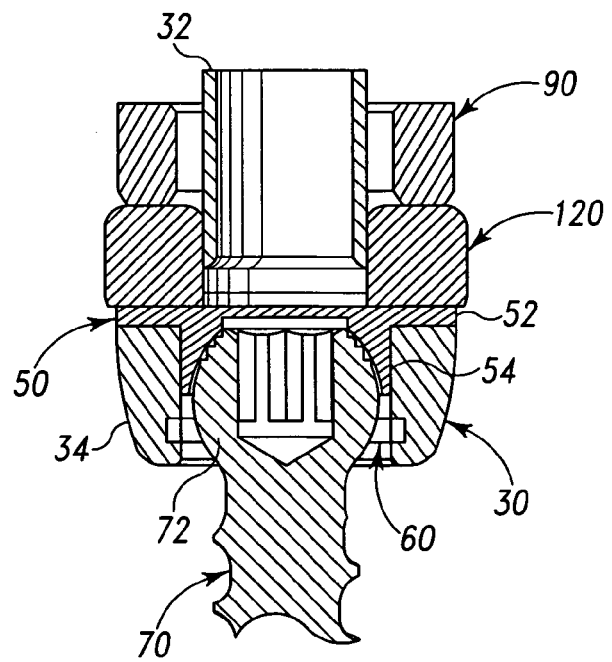
FIG. 14 is a sectional view through line 14-14 of FIG. 13.

Referring now to FIGS. 1-5 there is shown a multi-axial anchor assembly 20 having a first orientation aligned along longitudinal axis 21. Anchor assembly 20 includes a coupling member 30 and an anchor member 70 pivotally engaged to coupling member 30 with a clip 60. Anchor member 70 is pivotal about longitudinal axis 21 to a desired orientation relative thereto. A crown 50 is received in coupling member 30 adjacent anchor member 70, and includes at least seat portion that extends outwardly from coupling member 30 through windows 48. Crown 50 is positionable against a lower surface of a plate member positioned about coupling member 30, and a locking member 90 (FIG. 10) is engageable to coupling member 30 to secure the plate member against crown 50, as shown in FIG. 14. The downwardly or distally directed securing force supplied by engagement of locking member 90 can also seat crown 50 on anchor member 70 to rigidly engage anchor member 70 in the desired position relative to coupling member 30.

Figure 6:
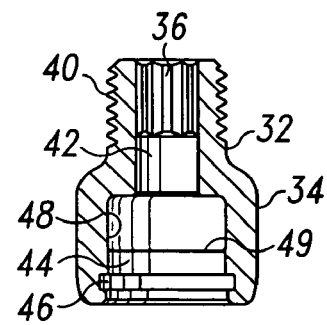
FIG. 6 is a sectional view of a coupling member comprising a portion of the anchor assembly of FIG. 1.

Further features of coupling member 30 will now be discussed with reference to FIGS. 1-6. Coupling member 30 includes a proximally extending post 32 and a lower receiver portion 34 centered about longitudinal axis 21. Post 32 includes a reduced size relative to receiver portion 34 so that post 32 can pass through an opening of the plate member while at least a portion of the receiver portion 34 is sized to prevent passage through the opening of the plate member. As shown in FIG. 6, coupling member 30 includes an upper passage portion 42 extending through post 32 in communication with a receptacle 44 defined in receiver portion 34. Receiver portion 34 includes an inner circumferential groove 46 adjacent receptacle 44 for receiving and retaining clip 60 therein.

Figure 3:
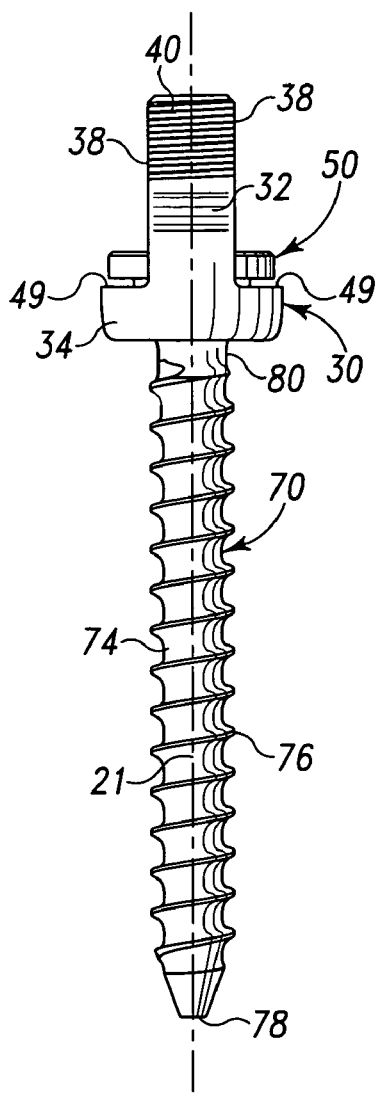
FIG. 3 is an assembled elevational view of the anchor assembly of FIG. 1.
Figure 4:
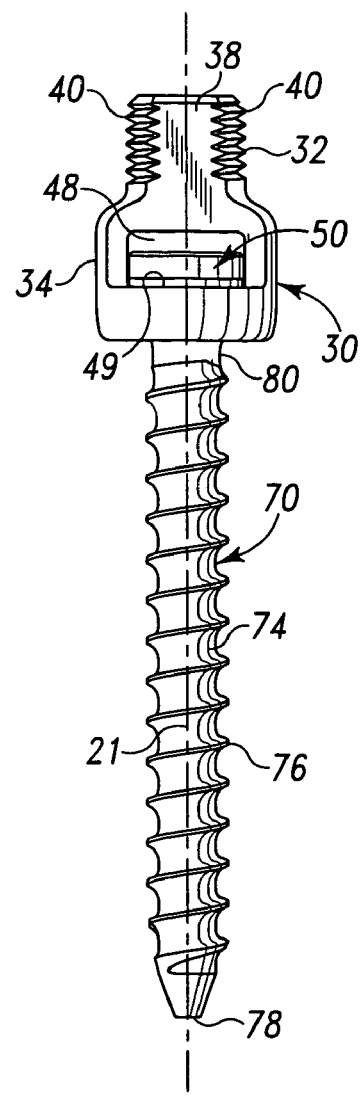
FIG. 4 is an assembled elevational view of the anchor assembly of FIG. 1 rotated 90 degrees about its longitudinal axis from its FIG. 3 orientation.
Figure 5:
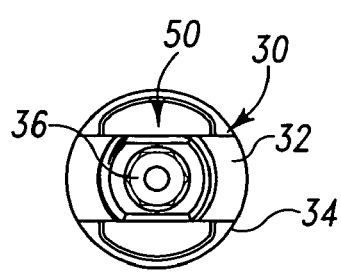
FIG. 5 is a top plan view of the anchor assembly of FIG. 4.

Receiver portion 34 further includes at least one opening so that crown 50 communicates with the exterior of coupling member 30. In the illustrated embodiment, coupling member 30 defines windows 48 in opposite sides thereof in communication with receptacle 44. As discussed further herein, at least a portion of crown 50 projects through windows 48 for contact with a plate member positioned about post 32. Crown 50 is sized to project outwardly from post 32 so that the plate member positioned thereabout will be supported by crown 50. Furthermore, as shown in FIG. 3, post 32 includes opposite flats 38 and opposite arcuate threaded portions 40 extending therebetween. As discussed below and shown in FIG. 14, flats 38 engage the sides of an elongated slot or other opening in the plate member. In one embodiment, post 32 prevents the plate member from twisting or rotating about post 32 by engaging the sides of an elongate slot of the plate member. Threaded portions 40 threadingly engaging a locking member 90 positioned about post 32.

Upper passage portion 42 of post 32 defines a proximally opening tool engaging passage 36 with internal surfaces forming a non-circular cross-section configured to engage a tool to facilitate rotating coupling member 30 about longitudinal axis 21. In addition, passage portion 42 can be sized to permit passage of a driving instrument to engage the anchor member captured in receiver portion 34 and apply a driving force directly to the anchor member through coupling member 30.

Referring now to FIG. 7, a sectional view of crown 50 is shown. Crown 50 includes a seat portion 52 having arms 53 extending from a lower cup portion 54. As shown in FIG. 1, seat portion 52 forms an oval shape with linear wall portions 57 extending between arms 53. Cup portion 54 includes a semi-spherical shape projecting from seat portion 52 with an opening formed at its lower or distal end 55. Cup portion 54 defines a receptacle 58 having a concavely curved inner surface adapted to receive the shape of the head of anchor member 70 positioned in coupling member 30. A through-hole 56 extends through seat portion 52 and is in communication with the receptacle 58 in cup portion 54, allowing placement of a driving instrument therethrough for engagement with a tool recess in the head of the anchor member 70 positioned in receptacle 58.

FIG. 8 shows another embodiment crown 250 having an upper or proximal seat portion 252 and a lower or distal cup portion 254. Cup portion 254 defines a receptacle which extends from seat portion 252 and opens distally opposite seat portion 252. The head of the anchor member 70 is received in the receptacle defined by cup portion 254. At least a portion of seat portion 252 is formed by a pair of outwardly projecting arms 253 extending proximally and distally along cup portion 254. A through-hole 256 extends through seat portion 252 and is in communication with the receptacle defined by cup portion 254.

FIG. 9 shows another embodiment crown 350, which is similar to crown 50. Crown 350 includes an upper or proximal seat portion 352, a lower or distal cup portion 354 and a through-hole 356. Arms 353 extend outwardly from cup portion 354, and include flange members 358 extending distally therefrom at the outer ends of respective ones of the arms 353. The distal end of each flange member 358 includes inwardly facing lip 359. In use, lips 359 are supported on window ledges 49 of coupling member 30 with the anchor member 70 pivotally captured in receiver portion 34. Flange members 358 and lips 359 maintain clearance between the head of the anchor member 70 positioned adjacent crown 350 so that when the plate member is secured against seat portion 352, flange members 358 and lips 359 maintain clearance between the head of the anchor member 70 and crown 350 so that the anchor member 70 can pivot in coupling member 30. Crown 350 may be employed in situations where dynamic stabilization of one or more vertebrae is desired. Dynamic stabilization can also be provided by any one or combination of removing the ridges 82 from the head 72 of the anchor member 70 (FIG. 11), providing a resilient crown member, or maintaining separation between the crown member and the head of the anchor member.

FIG. 10 shows one embodiment of a locking member 90 engageable to post 32 of coupling member 30. Locking member 90 includes a body 92 having a sidewall 96 extending about a threaded through-bore 94. Through-bore 94 extends along a longitudinal axis 95 that is alignable along the longitudinal axis 21 of anchor assembly 20. A slot 98 extends through sidewall 96 and is communication with through-bore 94, separating locking member 90 into proximal and distal portions 91, 93. When locking member 90 is engaged about post 32 and the distal portion is in contact with the plate member 120, as shown in FIG. 14, further tightening of locking member 90 against the plate member causes the proximal portion 91 to deflect toward the distal portion 93. This provides an interference fit or cross-threading between threads of post 32 and the threads of locking member 90, preventing locking member 90 from loosening in situ. Other embodiments contemplate other forms for locking members 90, including a locking member without slot 98, a locking member with break-off portions to ensure proper torque is applied during engagement, or a locking member providing other engagement relationships with post 32, such as a bayonet-lock, interference fit, or fused connection.

Figure 11:
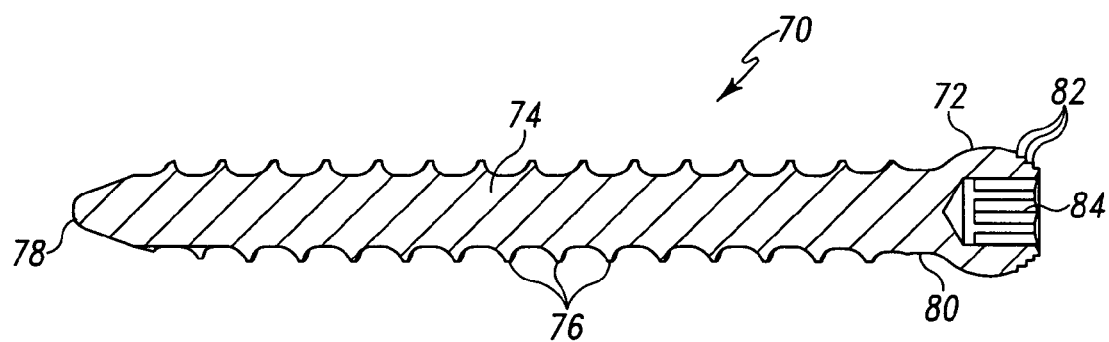
FIG. 11 is a section view of a first embodiment anchor member of the anchor assembly of FIG. 1.

FIG. 11 shows one embodiment of anchor member 70. Anchor member 70 includes enlarged head 72 at a proximal end thereof, and a distal portion that includes a threaded shaft 74 extending distally from head 72 to a tapered distal tip 78.

Shaft 74 includes a thread profile 76 extending therealong configured to engage bony tissue. Shaft 74 and thread profile 76 may include any suitable form, including flutes along all or a portion of shaft 74, and uniform or varying thread pitches, thread heights, thread widths, and shapes along shaft 74. Thread profile 76 can be configured for insertion into a drilled and tapped hole, can be configured as a self-tapping thread, or can be configured as a self-drilling and self-tapping thread. A non-threaded neck 80 is provided between head 72 and shaft 74, although threads may extend along and/or run-out along neck 80. Head 72 further includes a tool engaging recess 84 opening at the proximal end thereof that can include any suitable configuration for receiving a driving tool to apply a rotational driving force to anchor member 70 and threadingly engage it to bony tissue.

Head 72 includes plurality of ridges 82 extending circumferentially therearound adjacent the proximal end thereof, although a head 72 without ridges 82 is also contemplated as discussed above. For example, dynamic stabilization of the spinal column segment can be provided with an anchor member having a smooth head that is allowed to rotate in crown 50 when the anchor assembly is engaged to the plate member with locking member 90. Ridges 82, as discussed further herein, engage or bite into crown 50 to lock anchor member 70 in position relative to coupling member 30 when engaged to a plate member with locking member 90. Ridges 82 can be formed by a series of flattened surfaces machined into head 72. Other embodiments contemplate ridges 82 formed by spikes, knurlings, teeth, or other surface features. An anchor assembly 20 having an anchor member with ridges 82 provides a rigid or static connection between the plate member and the spinal column segment.

For any implant, it can be entirely statically engaged to the spinal column with anchor assemblies 20 having anchor members that are rigidly engaged with the respective coupling member secured to the implant. Any implant can be entirely dynamically engaged to the spinal column with anchor assemblies 20 having anchor members that are pivotal in the respective coupling members secured to the implanter. Combinations of rigid and dynamic anchor assemblies 20 can be employed to engage an implant to the spinal column.

Figure 12:
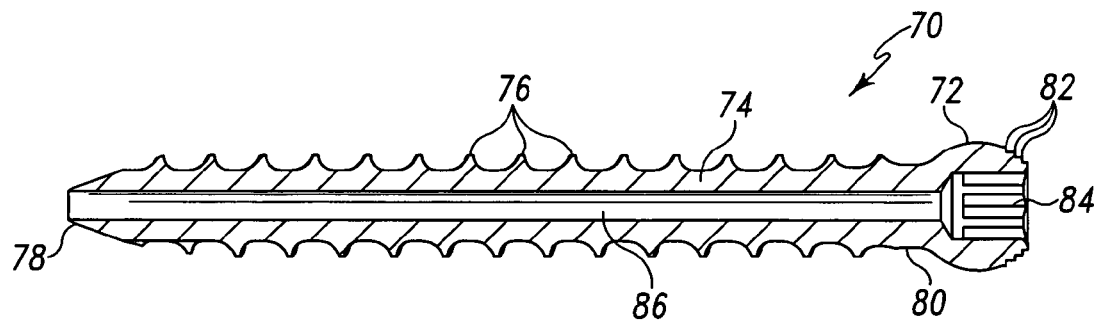
FIG. 12 is a sectional view of another embodiment anchor member of the anchor assembly of FIG. 1.

Referring to FIG. 12, there is shown another embodiment of anchor member 70 in which shaft 74 is provided with a lumen 86 extending longitudinally therealong and opening at distal tip 78 and into tool engaging recess 84. Lumen 86 can be configured to receive a guidewire or other guiding member to guide placement of anchor member 70 to the desired location relative to the bony structure. Lumen 86 can also be employed to deliver bone graft or other bone growth promoting and/or therapeutic material into the bony structure in which anchor member 70 is engaged. Still other embodiments contemplate shaft 74 including one or more fenestrations or openings in communication with lumen 86 that are located between neck 80 and distal tip 78.

Still other embodiment contemplate that anchor member 70 includes a distal portion with other configurations for engaging bony tissue. For example, the distal portion may include a cable, a hook, a clamp, a staple, a smooth shaft with wings or gulls, an expandable anchor, a body for positioning in a disc space between vertebrae, or other structure for engaging bony structure.

Figure 13:
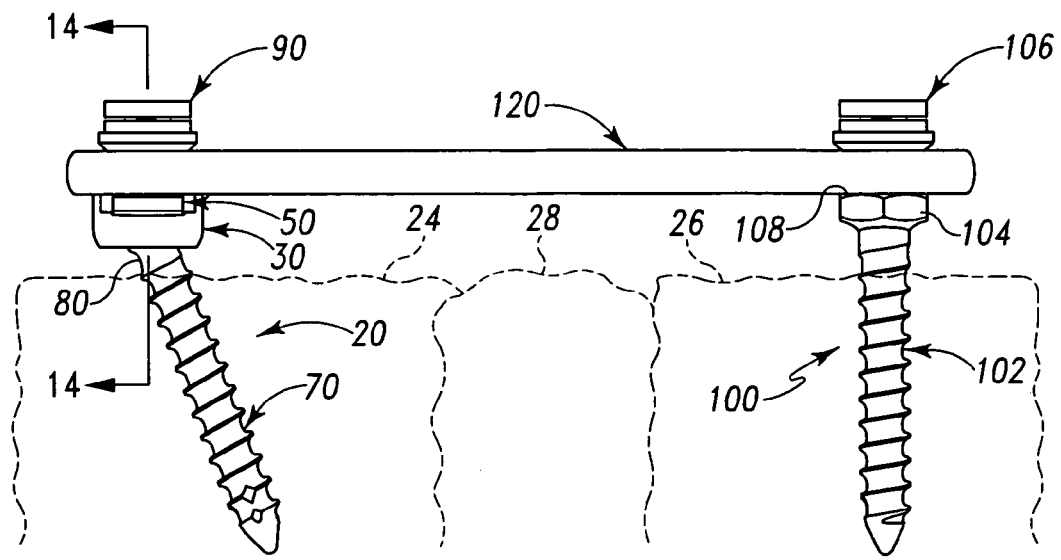
FIG. 13 is an elevational view of a plate member secured to the multi-axial anchor assembly of FIG. 1 with the locking member of FIG. 8, and with the plate member secured to an uni-axial anchor.

Referring now to FIG. 13, there is shown an elongate plate member 120 engaged to vertebrae 24, 26 on opposite sides of disc space 28 with a multi-axial anchor assembly 20 and an uni-axial anchor 100. It should be understood that plate member 120 can be engaged to the vertebrae with any combination of multi-axial and/or uni-axial anchor assemblies. Uni-axial anchor assembly 100 includes a threaded shaft member 102 and a proximal head member 104 extending therefrom that is integrally formed therewith. Proximal head member 104 extends through plate member 120, and includes a lower support member 108 against which the lower surface of plate member 120 is positioned. A locking member 106 is engaged to head member 104 and clamps or seats plate member 120 against lower support member 108.

The connection of plate member 120 with multi-axial anchor assembly 20 is also shown in section view in FIG. 14. Plate member 120 is positioned so that its lower surface is in contact at least partially with seat portion 152 of crown 150. Post 32 of coupling member 130 extends through plate member 120, and locking member 90 is positioned about post 32. As locking member is advanced along post 32 toward the upper surface of plate member 120, locking member 90 exerts a force against plate member 120 and firmly secures it between seat portion 52 of crown 50 and locking member 90. In the illustrated embodiment, the securing force pushes crown 50 downwardly against head 72 of anchor member 70. For embodiments contemplating rigid fixation, the anchor member 70 includes ridges 82 that bite into crown 50 to lock anchor member 70 in position relative to coupling member 30 and plate member 120.

Referring now to FIGS. 15-17, further details of one embodiment of plate member 120 are shown. Plate member 120 includes an elongate body 122 extending along a longitudinal axis 121. Body 122 includes at least one opening in the form of an elongate slot 124 centered and extending along longitudinal axis 121. Slot 124 opens at upper and lower surfaces 125, 127. Side rails 126 extend longitudinally along opposite sides of slot 124, and end rails 128 extend between side rails 126 at the ends of body 122.

Side rails 126 include an inner surface 129 extending along slot 124 and an outer surface 131. As shown in FIG. 17, body 122 includes longitudinal grooves 130 in inner surface 129 extending along slot 124. The plate surfaces and edges of rails 126, 128 transitioning between the upper and lower plate surfaces and between the inner and outer rails surfaces can be rounded or chamfered to eliminate any sharp edges or abrupt transitions between plate surfaces.

In FIG. 18, there is shown plate member 120 with a curved profile along its longitudinal axis 121. Upper surface 125 is concavely curved, and lower surface 127 is convexly curved. The curved configuration can be provided by pre-bent plates, or by the surgeon bending the plate during surgery to provide the desire fit with the patient's anatomy.

In FIG. 19, there is shown another embodiment plate member 140. Plate member 140 is similar to plate member 120, and includes an elongated body 142 having opposite side rails 146 and opposite end rails 148. Plate member 140 includes openings in the form of a pair of elongated slots 144, 145 are formed along body 142, and intermediate rail 150 is located between slots 144, 145 and extends between side rails 146. In the illustrated embodiment, slot 144 is shorter than slot 145. Other embodiments contemplate slots of equal length, and plate members with more than two slots. For any of the plate member embodiments, the slots may include scallops, recesses or other features to facilitate placement or engagement of anchors therewith. It is also contemplated that the plate members may include two or more slots adjacent to and extending along one another. Still other embodiments contemplate the plate members are provided with openings between the upper and lower surfaces in the form of circular holes.

In FIG. 20 there is shown another embodiment plate member 160. Plate member 160 includes a body member 162 having side rails 166 and end rails 168. A pair of end slots 165 is provided adjacent end rails 168, and an intermediate slot 164 is provided between end slots 165 with intermediate rails 170 located between intermediate slot 164 and respective ones of the end slots 165. In the illustrated embodiment, intermediate slot 164 is longer than end slots 165.

Figure 21:
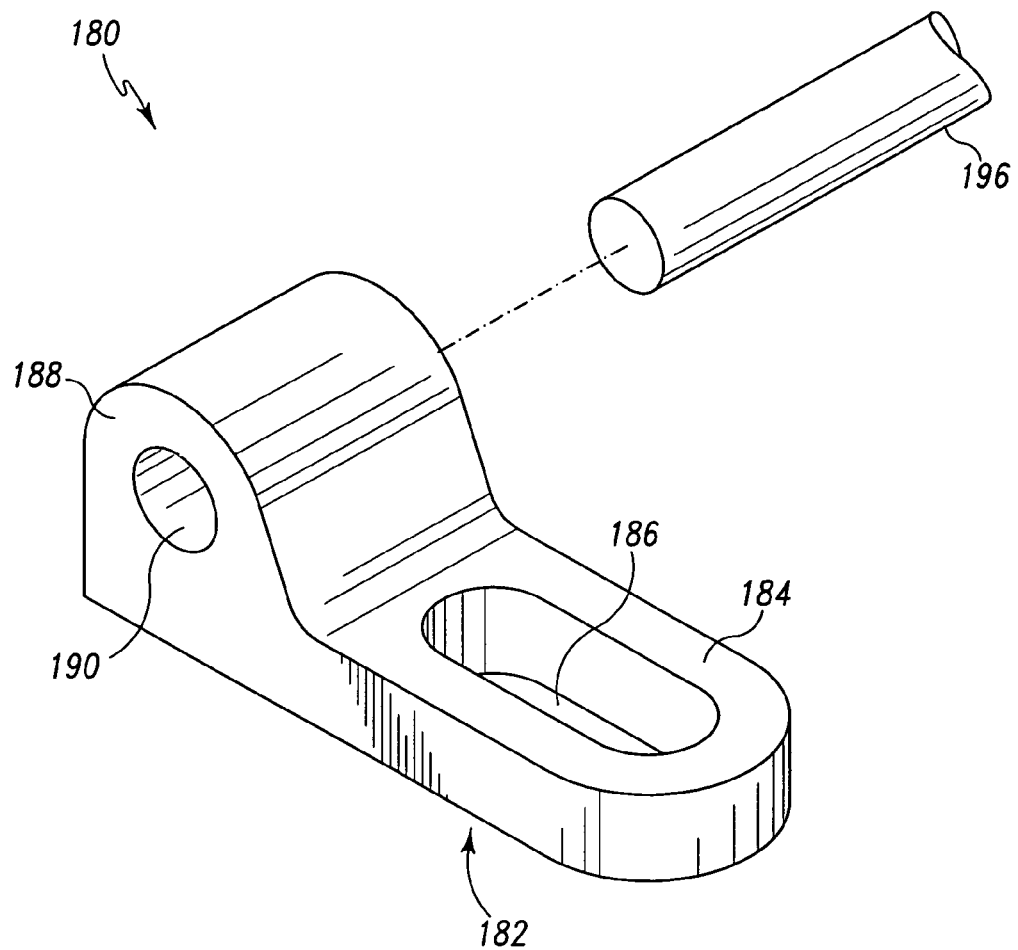
FIG. 21 is a perspective view of another embodiment plate member with a rod receiving portion.

In FIG. 21 there is shown another embodiment plate member 180. Plate member 180 includes a body 182 having an anchor assembly engaging portion 184 and a rod receiving portion 188. Anchor assembly engaging portion 184 includes an opening therethrough in the form of an elongate slot 186 for receiving an anchor assembly, such as anchor assembly 20. Slot 186 allows the positioning of the plate member 180 to be adjusted by securing it thereto with anchor assembly 20. Rod receiving portion 188 defines a passage 190 for receiving an elongate spinal rod 196 therein. Passage 190 extends transversely to slot 186. In the illustrated embodiment, rod receiving portion 188 is a cylindrical member that completely surrounds passage 190. However, other embodiments contemplate a passage that is open along all or a portion of a side thereof, a rod receiving portion 188 comprising multiple components for clamping or gripping the rod in passage 190, and other suitable arrangements for receiving and/or engaging a rod or other elongate implant member.

Figure 22A:
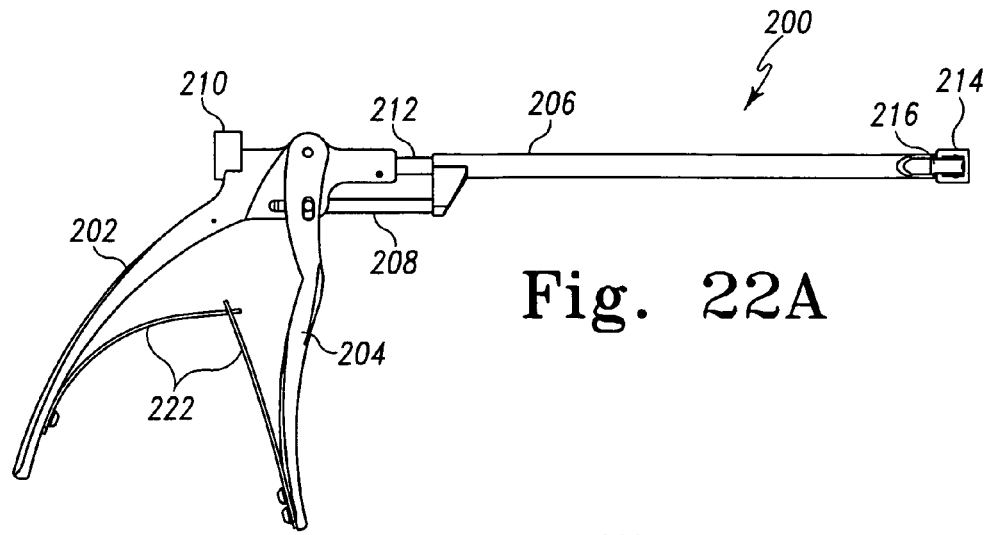
FIG. 22A is an elevation view of an instrument for holding a plate member.
Figure 22B:
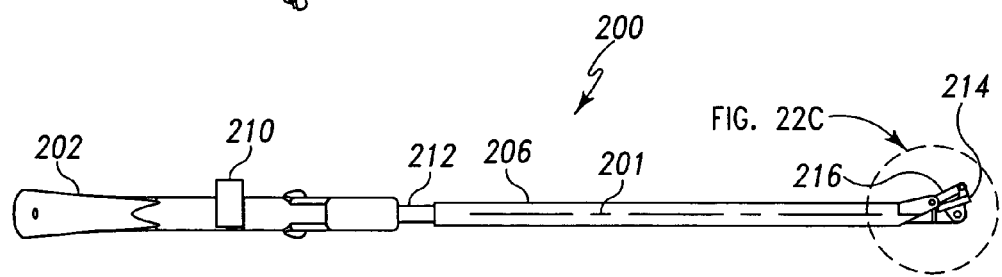
FIG. 22B is a top view of the instrument of FIG. 22A.
Figure 22C:
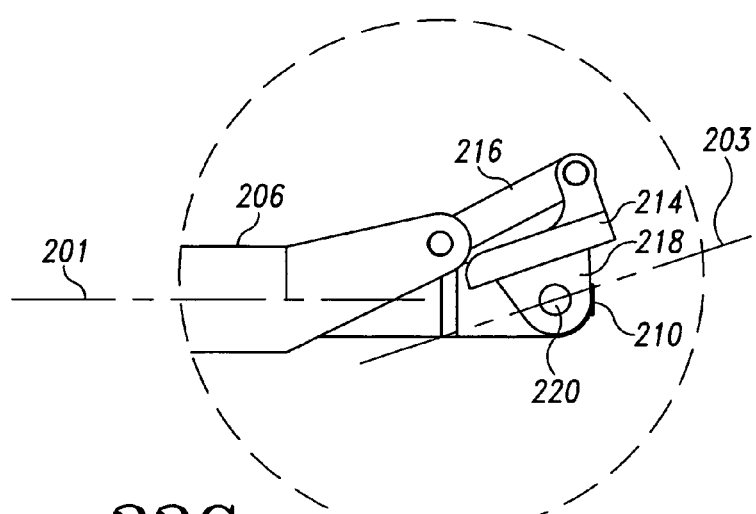
FIG. 22C is an enlarged view of a distal holding portion of the instrument of FIG. 22A in a first orientation.

FIGS. 22A-22E show one embodiment plate holder 200 engageable in, for example, grooves 130 to hold the plate member for delivery to the operative site. Examples of holding instruments are provided in U.S. patent application Ser. No. 10/202,918 filed on Jul. 25, 2002, which is incorporated herein by reference in its entirety. Plate holder 200 includes a handle member 202 and a lever member 204 pivotally coupled thereto. A shaft member 206 is coupled to lever member 204 with a first link 208. A mounting shaft 212 extends through shaft member 206 from handle member 202, and includes a locking member 210 having a proximal knob portion and a shaft extending through mounting shaft 212, as shown in FIG. 22C.

The distal end of mounting shaft 212 includes a mounting member 214 pivotally mounted thereto. Mounting member 214 includes an engaging portion 218 sized to fit within, for example, slot 124 of plate member 120. Engaging portion 218 can also be sized to fit within an opening or slot of any plate member embodiment discussed herein. In the illustrated embodiments, engaging portion 218 includes engaging members 220 to engage groove 130 of plate member 120. Engaging members 220 can be in the form of ball members or stems that can recess into engaging portion 218 for positioning in slot 124, and can then be moved outwardly to engage groove 130 and mount plate member 120 to mounting member 214. Locking member 210 can then be rotated within mounting shaft 212 by its proximal knob so that its distal end portion in engaging portion 218 secures engaging members 220 in engagement with the plate member.

Figure 22D:
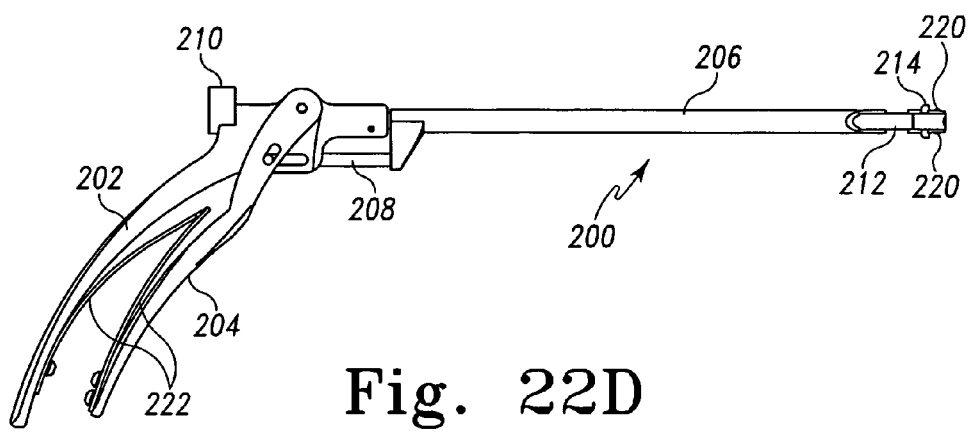
FIG. 22D is an elevation view of the instrument of FIG. 22A with the holding portion in a second orientation.
Figure 22E:
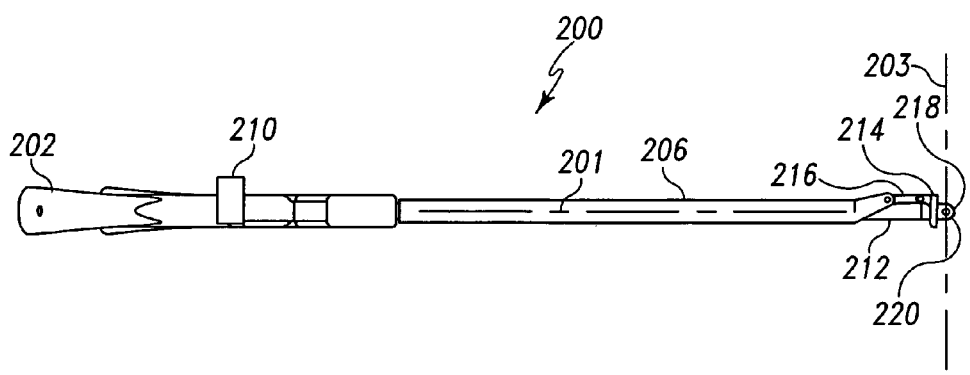
FIG. 22E is a top view of the instrument of FIG. 22A with the holding portion in the second orientation.
Figure 23:
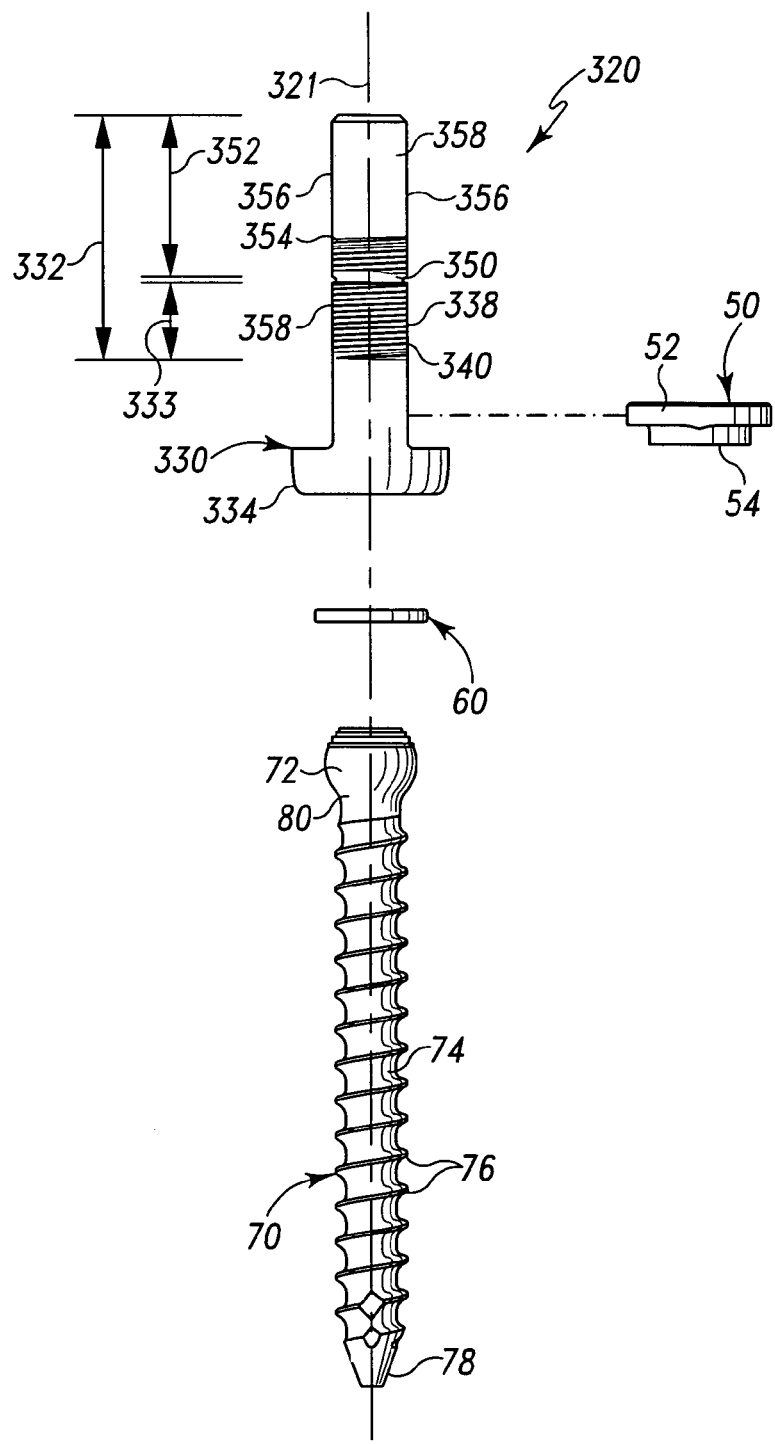
FIG. 23 is an exploded elevation view of another embodiment multi-axial anchor assembly.

Shaft member 206 is movable relative to handle member 202 and mounting shaft 212 by moving lever 204 between an open position as shown in FIG. 22A and a closed position as shown in FIG. 22D. Spring mechanism 222 normally biases lever member 204 and handle member 202 to the open position. In the open position, mounting member 214 is oriented so that the plate member extends along an axis 203 (FIG. 22C) which is oriented more along the longitudinal axis 201 of instrument 200. In the closed position, link 216 extending between shaft member 206 and mounting member 214 pivots mounting member 214 about the distal end of mounting shaft 212 as shaft member 206 is moved proximally with lever 204. In the closed position, axis 203 and thus the plate member secured to mounting member 214 extend perpendicular to or substantially transversely to the longitudinal axis 201 of instrument 200. Thus, instrument 200 facilitates placement of the plate through narrow incisions or tubes by holding the plate in a first orientation that is oriented along the approach to the spinal column and thereafter allowing the plate to be remotely pivoted into alignment along the spinal column.

Instrument 200 is just one example of a suitable instrument for holding and delivering plate members to the spinal column for engagement thereto with the anchor assemblies discussed herein. Other examples of holding instruments include forceps or other grasping instruments, instruments with fasteners to engage the plate, and instruments that provide an interference fit with the plate. The instruments can engage in the plate slots or holes, clamp between the outer surfaces of the plate, or hold the plate between a slot or hole surface and an outer surface of the plate, for example. Still other examples contemplate the plate is manually grasped and delivered to the surgical site.

Referring now to FIGS. 23-26, there is shown another embodiment multi-axial anchor assembly 320. Anchor assembly 320 includes a coupling member 330 with a post 332 extending along longitudinal axis 321 of anchor assembly 320. Post 332 is extended proximally from a receiver portion 334 a sufficient length along longitudinal axis 321 to facilitate positioning of an implant about the coupling member 330 and ease intra-operative assembly. Multi-axial anchor assembly 320 may also include post 332 having a removable proximal extension portion to provide a low profile when implanted.

In the illustrated embodiment, anchor assembly 320 includes anchor member 70 that is pivotally captured in coupling member 330 with clip 60. Crown 50 can be positioned in coupling member 330 about head 72 of anchor member 70. Seat portion 52 of crown 50 is exposed through the coupling member 330 so that a bottom surface of an implant such as a plate member received over post 332 and positioned thereagainst can be secured to anchor assembly 320 with a locking member 90 as discussed above with respect to anchor assembly 20.

Figure 24:
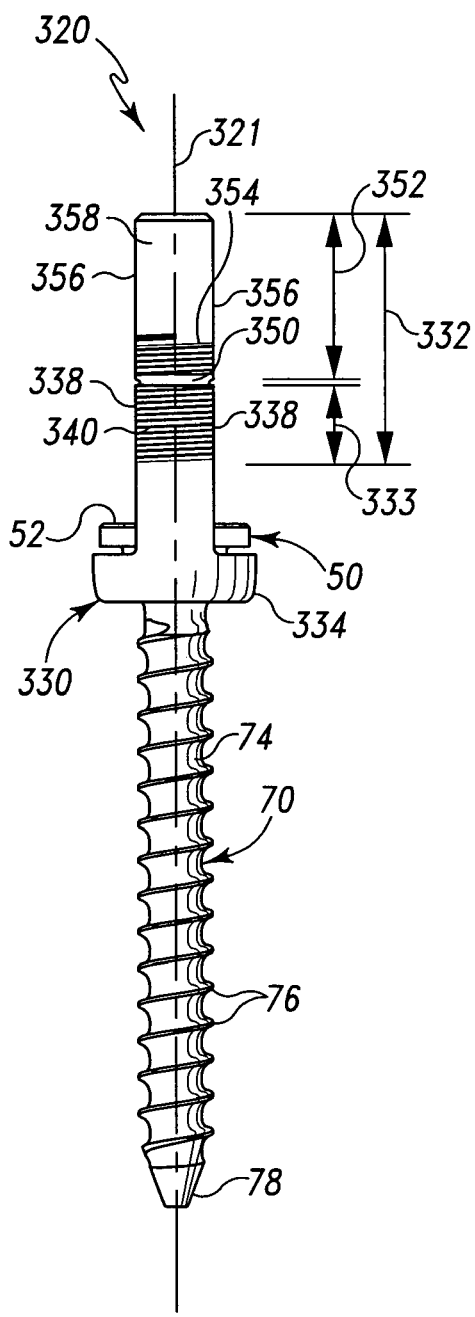
FIG. 24 is an elevational view of the anchor assembly of FIG. 23.

Coupling member 330 includes receiver portion 334 at a lower or distal end of post 332. Receiver portion 334 includes a receptacle 344 for receiving head 72 of anchor member 70 therein, and an internal circumferential groove 346 for receiving C-shaped clip 60. Clip 60 pivotally supports head 72 in receptacle 344, and cup portion 54 of crown 50 is positioned in receptacle 344 about head 372 so that at least a portion of seat portion 52 extends through opposite windows 348, as shown in FIG. 24.

Post 332 includes a locking member mounting portion 333 and an extension portion 352 extending proximally from mounting portion 333. Extension portion 352 provides a proximal extension of post 332 along longitudinal axis 321 that facilitates placement of an implant member thereover and to guide the implant to a location adjacent receiver portion 334 and crown 50 during surgery. Also, extension portion 352 prevents the implant from slipping off of post 332 as the implant and vertebrae are manipulated during surgery and before engagement of the locking member 90 to post 332. In addition, locking member 90 may be provisionally engaged to post 332 about extension portion 352, allowing sufficient space between crown 50 and locking member 90 for manipulating the implant into position relative to anchor assembly 320 during surgery prior to securement of the implant to anchor assembly 320 with locking member 90.

Figure 25:
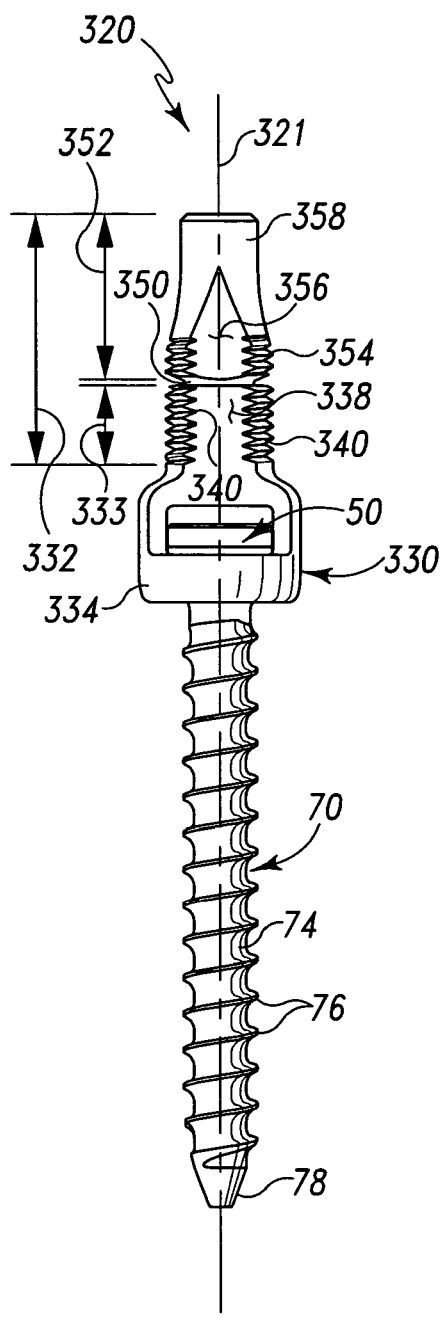
FIG. 25 is an elevational view of the anchor assembly of FIG. 24 rotated 90 degrees about its longitudinal axis.
Figure 26:
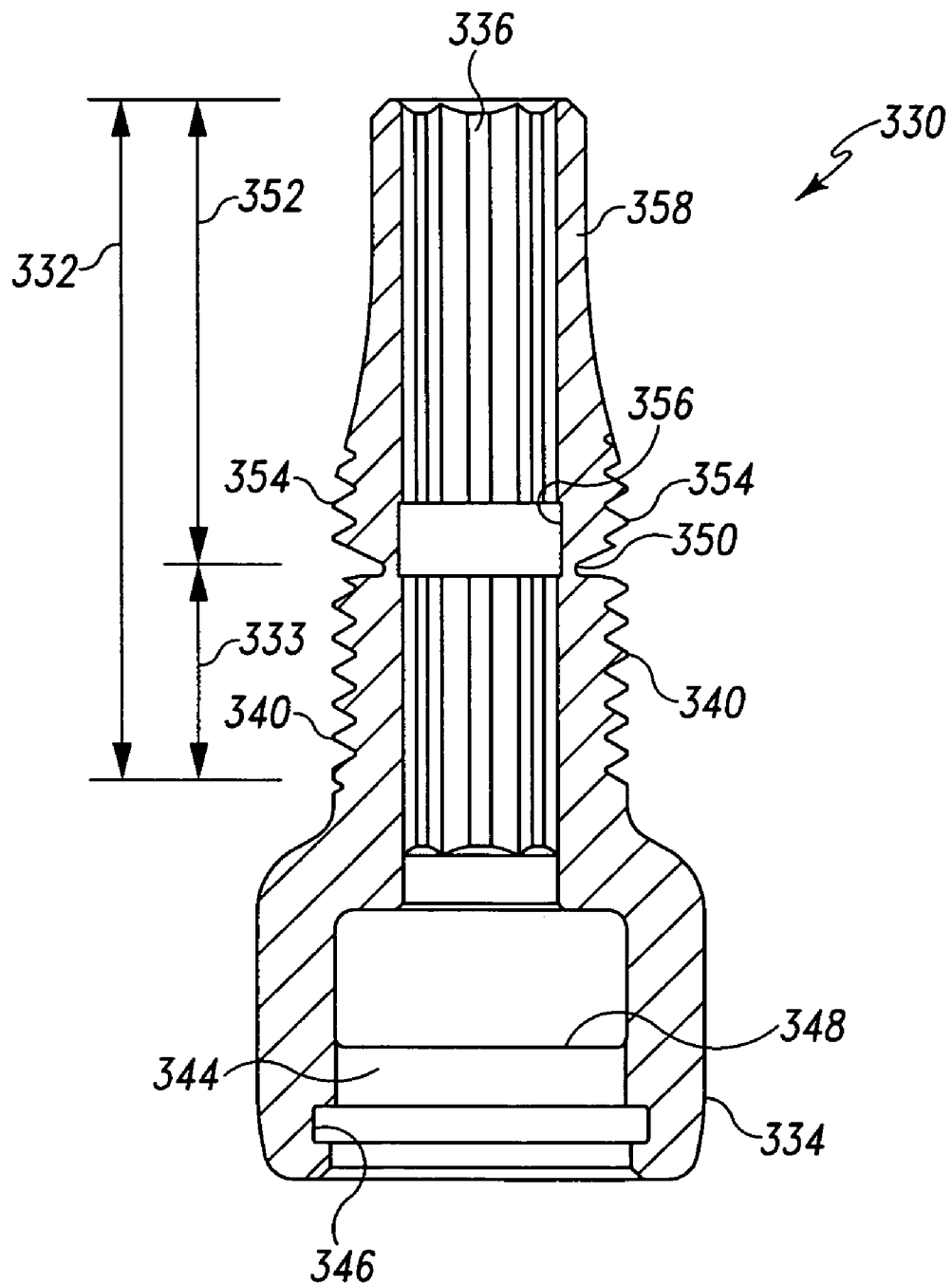
FIG. 26 is a sectional view of a coupling member comprising the anchor assembly of FIG. 23.

A break-off region 350 is provided between mounting portion 333 and extension portion 352. As shown in FIG. 26, break-off region 350 can be formed by inwardly tapering wall portions in post 332 that interrupt the thread profile along post 332 and also interrupt the surfaces forming flats 356 (FIG. 25.) A tool engaging passage 336 extends through extension portion 352 and mounting portion 333, and includes tool engaging surfaces that define a non-circular cross-section. A gauge portion 356 is provided in an inner wall surface of post 332 adjacent break-off region 350. Gauge portion 356 reduces the wall thickness of post 332 adjacent break-off region 350 so that a predetermined level of torque applied to extension portion 352 in tool engaging passage 336 proximally of break-off region 350 will sever extension portion 352 from mounting portion 333. The amount of torque required can be varied by varying the thickness of the wall of post 332 at break-off region 350.

Extension portion 352 includes a tapered proximal end 358 to further facilitate placement of the plate member thereabout. Extension portion 352 includes opposite flats 356 and threaded arcuate portions 354 extending between flats 356. Similarly, mounting portion 333 includes opposite flats 338 and threaded arcuate portions 340 extending therebetween aligned with the respective flats 356 and arcuate portions 354 of extension portion 352. Threaded arcuate portions 340, 354 threadingly receive and engage locking member 90 to post 332. Flats 338, 356 are sized to abut the sidewalls along the elongate slot or other opening of the plate member positioned thereover to eliminate lateral movement or pivoting of the plate member. Coupling member 330 is further aligned relative to the opening of the plate member as the plate member is advanced along extension portion 352. In another embodiment, it is contemplated that post 332 is threaded along its entire length. In a further embodiment, all or a portion of post 332 is provided without opposite flats, but rather includes a circular cross-section. In still another embodiment, post 332 is non-threaded along extension portion 352.

Figure 27:
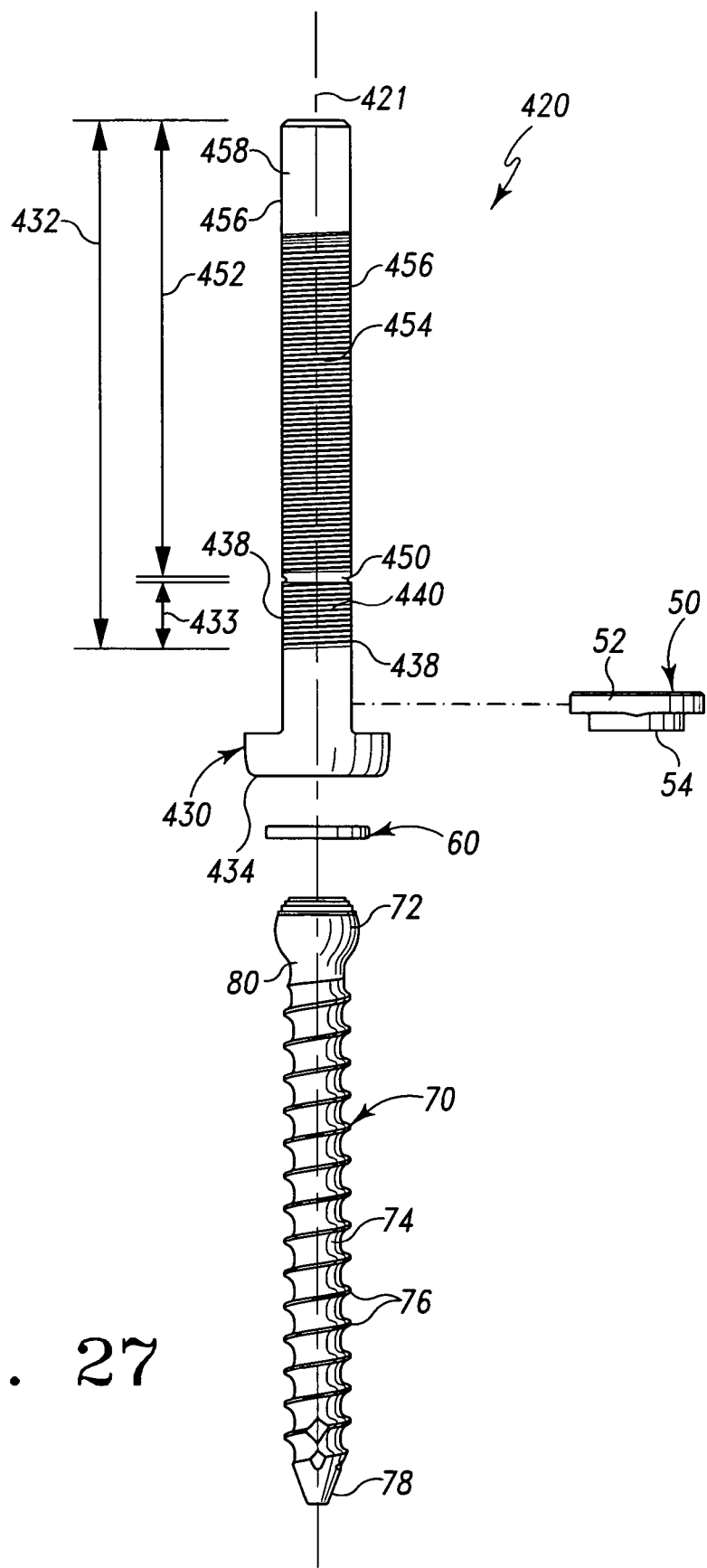
FIG. 27 is an exploded elevation view of another embodiment multi-axial anchor assembly.
Figure 28:
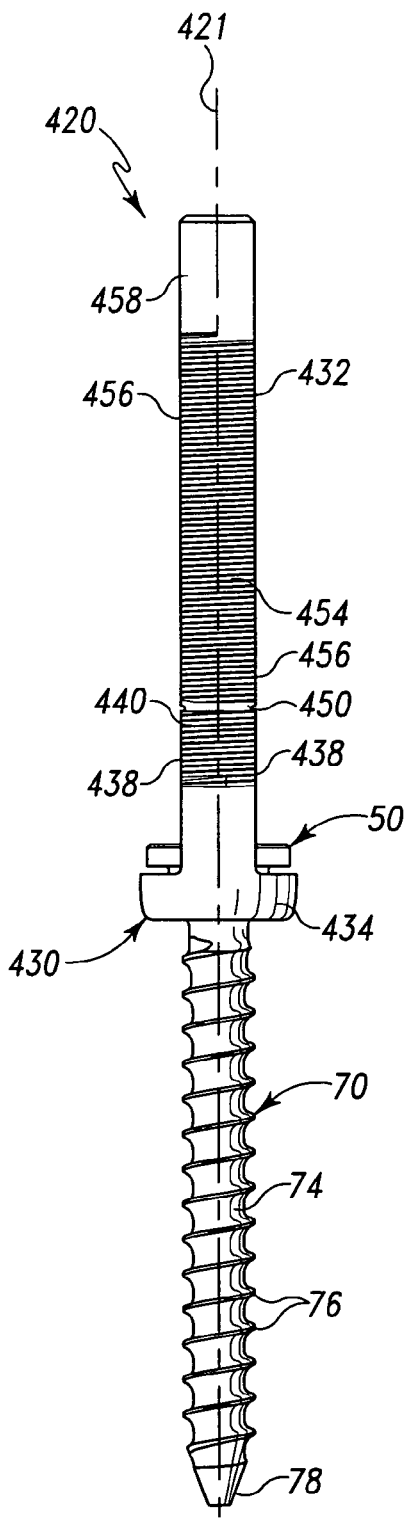
FIG. 28 is an elevational view of the anchor assembly of FIG. 27.
Figure 29:
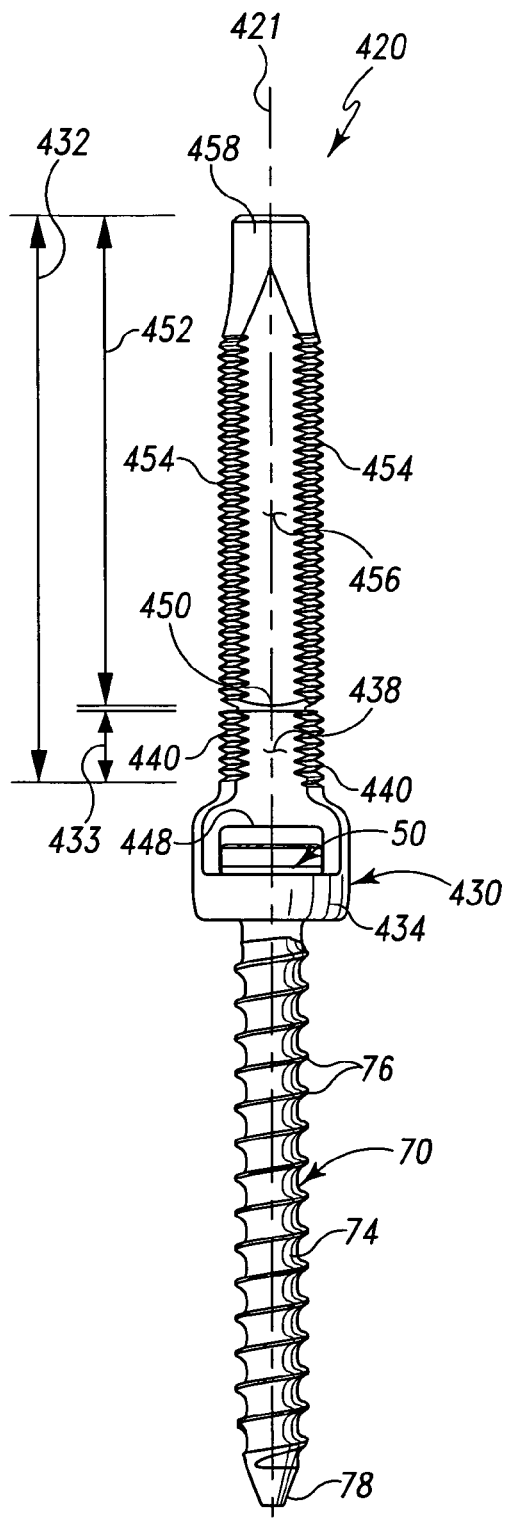
FIG. 29 is an elevational view of the anchor assembly of FIG. 28 rotated 90 degrees about its longitudinal axis.

Referring now to FIGS. 27-29, there is shown another embodiment multi-axial anchor assembly 420. Anchor assembly 420 includes a coupling member 430 with a post 432 extending along longitudinal axis 421 of anchor assembly 420. Anchor assembly 420 can include any suitable configuration as discussed above with respect to the other embodiment anchor assemblies. Extended post 432 is similar to extended post 332 of multi-axial anchor assembly 320, but includes a length along longitudinal axis 421 such that its proximal end is positioned adjacent to or extends through the incision or opening provided to access the spinal column. Extended post 432 facilitates positioning of an implant about the coupling member 430, and guides the implant through the incision to a location adjacent the vertebral body to which anchor member 70 is engaged. Surgical instruments for holding the implant can be eliminated, reducing crowding in the operative space formed by the incision.

In the illustrated embodiment, anchor assembly 420 includes an anchor member 70 that is pivotally captured in coupling member 430 with a clip 60. A crown 50 can be positioned in coupling member 430 about head 72 of anchor member 70. Seat portion 52 of crown 50 is exposed or extends through coupling member 430 such that a lower surface of the implant can be secured thereagainst as discussed above with respect to anchor assembly 20.

Coupling member 430 includes a receiver portion 434 at a lower or distal end of post 432. Receiver portion 434 can be configured as discussed above with respect to receiver portions 34 and 334. Post 432 includes a locking member mounting portion 433 and an extension portion 452 extending proximally from mounting portion 433. A break-off region 450 is provided between mounting portion 433 and extension portion 452. Extension portion 452 provides a proximal extension of post 432 that facilitates placement of an implant thereover and to guide the implant to a location adjacent crown 50 during surgery. Also, extension portion 452 prevents the implant from slipping off post 432 as the implant and vertebrae are manipulated during surgery and before engagement of the locking member 90 to post 432. In addition, locking member 90 may be provisionally engaged to post 432 about extension portion 452, allowing additional space for manipulating the implant into position relative to the anchor assemblies between crown 50 and locking member 90 during surgery and prior to securement of the implant to the anchor assembly with locking member 90.

Similar to anchor assembly 320, post 432 can be provided with an internal tool recess (not shown) extending through extension portion 452 and mounting portion 433, and a gauge portion in an inner wall surface thereof adjacent break-off region 450 so that a predetermined level of torque applied to extension portion 452 proximally of break-off region 450 will sever extension portion 452 from mounting portion 433.

Extension portion 452 includes a tapered proximal end 458 to further facilitate placement of the implant thereabout. Extension portion 452 includes opposite flats 456 and threaded arcuate portions 454 extending between flats 456. Similarly, mounting portion 433 includes opposite flats 438 and threaded arcuate portions 440 extending therebetween. Threaded arcuate portions 440, 454 threadingly receive and engage locking member 90. Flats 438, 456 are sized to abut the sidewalls along the elongate slot of other opening of the implant positioned thereover to eliminate lateral movement or pivoting of the implant, and to align coupling member 430 relative to the implant.

Extension portion 452 can facilitate rotation of coupling member 430 so that receiver portion 434 is properly aligned with the implant. Rotation of coupling member 430 can result due to the tapered proximal end portion 458 receiving the implant and self-aligning receiver portion 434 as the implant is moved distally along extension portion 452. Proximal end portion 458 can also be engaged by a tool or manually to rotate receiver portion 434 into the desired position relative to the implant.

For any embodiment anchor assembly discussed herein, and with specific reference to anchor assemblies 320, 420, posts 332, 432 can be engaged by a reduction instrument to provide a mechanical advantage in positioning the implant, such as a plate member, adjacent crown 50. Such reduction instruments can reduce the displacement between misaligned vertebrae, or can simply force the plate member into position adjacent the crown 50 prior to final securement with locking member 90. Still other embodiments contemplate that reduction of the plate member and/or vertebrae can be achieved by threading locking member 90 against the upper surface of the plate member to force the plate member adjacent crown 50.

For example, a plate member can be positioned about post 332, 432 and the locking member can be provisionally engaged to the post 332, 432 so that at a portion of the threaded arcuate portions 354, 454 are exposed proximally of the locking member. The reduction instrument can include a first member threadingly engaged to extension portion 352, 452 and a second member movable relative to the first member with an actuator. The second member can be positioned into contact with the plate member, and leveraged off the first member with the actuator to move the plate member along the post 332, 432 toward crown 50. The locking member 90 can then be advanced along the mounting portion 333, 433 to securely engage the plate member against the crown member while the reduction instrument holds the plate member in the desired position relative to the anchor assembly.

Figures 30, 31:
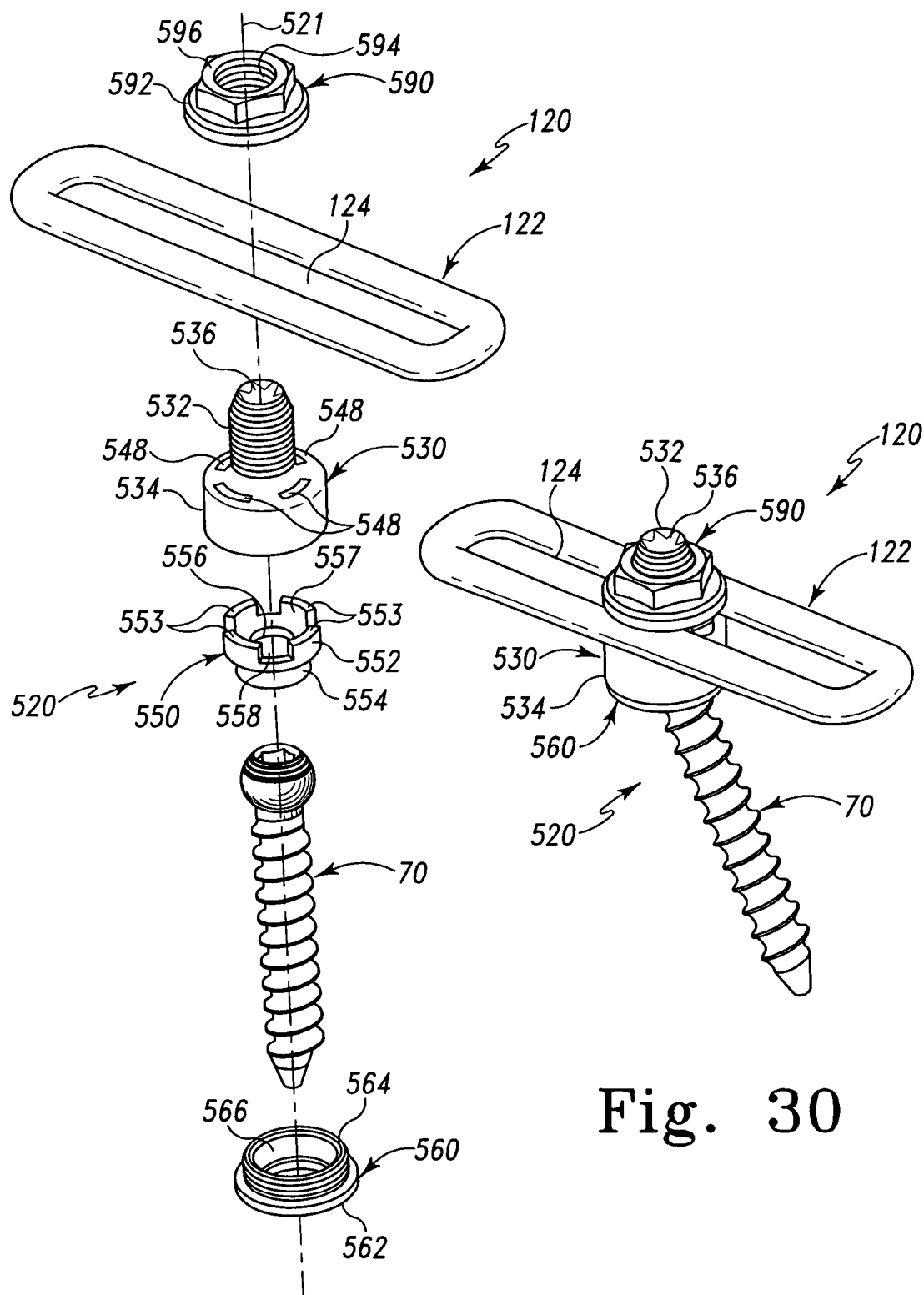
FIG. 30 is a perspective view of another embodiment multi-axial anchor assembly engaged to a plate member.
FIG. 31 is an exploded view of the plate member and anchor assembly of FIG. 30.
Figure 32:
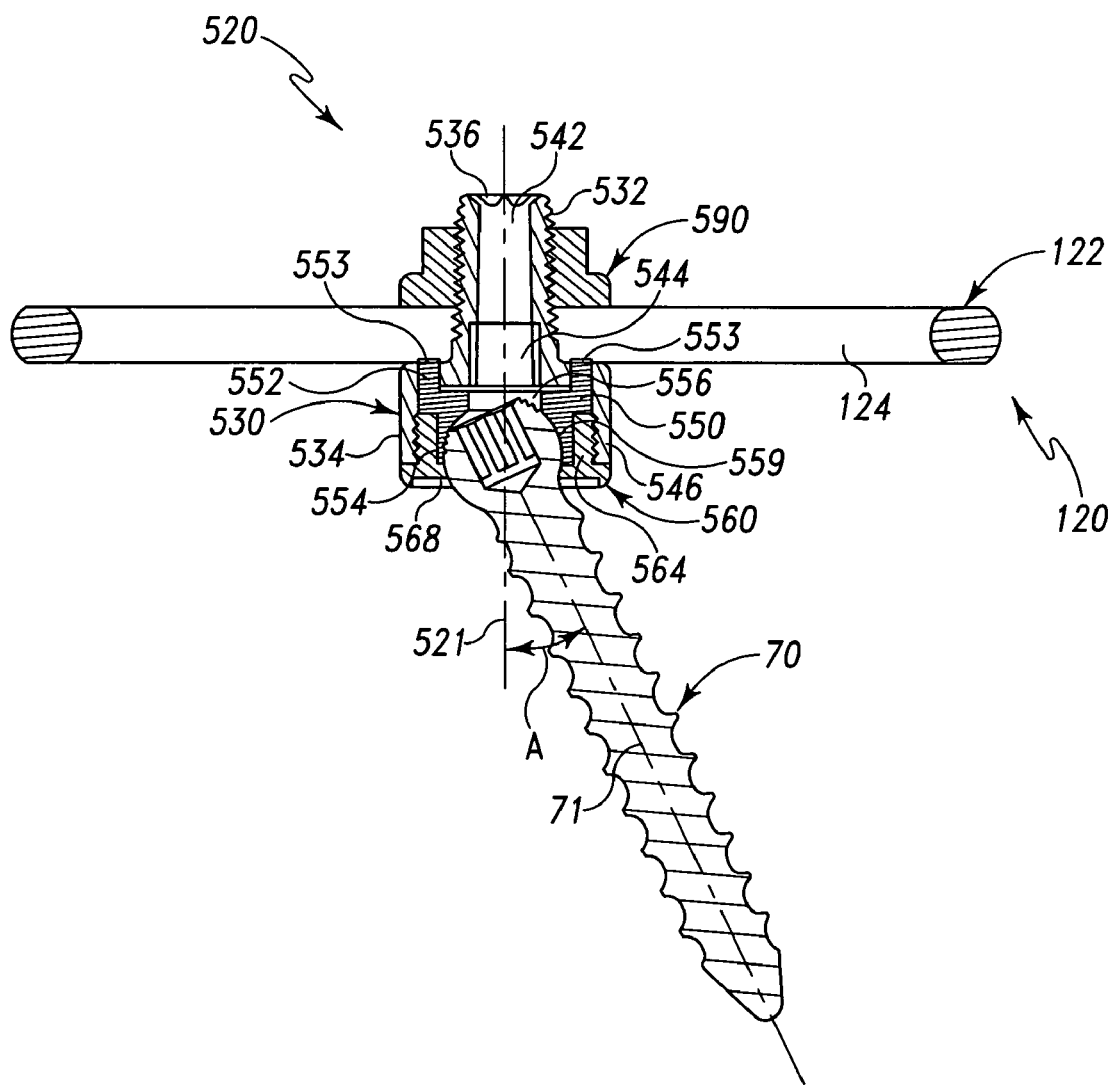
FIG. 32 is a cross-section view of the plate member and anchor assembly of FIG. 31.
Figure 32A:
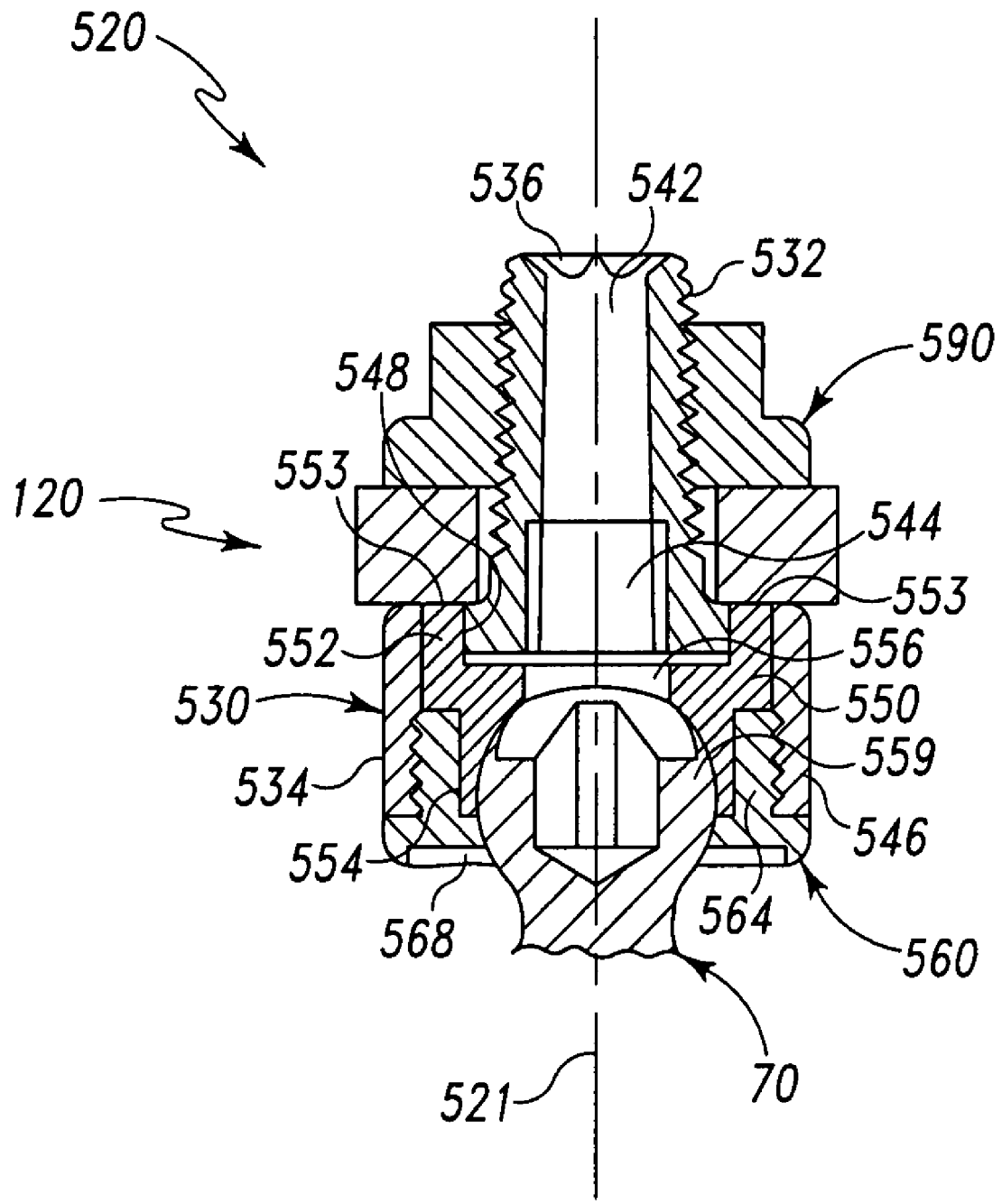
FIG. 32A is another cross-sectional view of the plate member and anchor assembly of FIG. 31 looking in a directional orthogonal to the direction of FIG. 32.

FIGS. 30-32 show another embodiment multi-axial anchor assembly 520 provided to secure an implant to one or more vertebrae of the spinal column. Anchor assembly 520 includes anchor member 70 pivotally coupled in a receiver portion 534 of a coupling member 530. Coupling member 530 includes a post 532 extending proximally from receiver portion 534 for receiving an implant, such as plate member 120 as shown, thereabout. Anchor member 70 is pivotal relative to the plate member 120 when post 532 is positioned through opening 124 of plate member 120. In one form, coupling member 530 includes a crown 550 in receiver portion 534 that extends between anchor member 70 and plate member 120 positioned about post 532. In one embodiment, crown 550 rigidly engages anchor member 70 in position relative to coupling member 530 and plate member 120 when locking member 590 is secured against plate member 120.

Coupling member 530 can include one or more windows to provide a path for crown 550 to communicate with the exterior of coupling member 530. In one embodiment, coupling member 530 includes at least one window 548 and crown 550 includes a seat portion 552 formed by at least one axially extending arm 553 projecting through the at least one window 548 for contact with plate member 120 when positioned about post 532. Locking member 590 firmly engages plate member 120 against one or more of the arms 553 of crown 550 when locking member 590 is positioned against plate member 120. In the illustrated embodiment, coupling member 530 includes four windows 548 spaced thereabout, and crown 550 includes four arms 553 defining seat portions 552 extending axially through respective ones of the four windows 548. Other embodiments contemplate an arrangement with two arms and windows, three arms and windows, or more than four arms and windows. The windows and arms can be evenly spaced from one another, or spaced at uneven intervals. It is further contemplated that the same number of arms and windows need not be provided for a particular anchor assembly.

Multi-axial anchor assembly 520 includes a first orientation wherein anchor member 70 and post 532 are aligned along longitudinal axis 521. Anchor assembly 520 further includes anchor member 70 pivotally engaged to coupling member 530 with a retainer clip 560 in the distally facing opening of receiver portion 534. Anchor member 70 is multi-axial and pivotal about longitudinal axis 521 to an infinite number of positions relative thereto within a cone extending about axis 521. In one embodiment, the angular range A defined by the cone extends up to 90 degrees from axis 521 to a longitudinal axis 71 of anchor member 70. In another embodiment, the angular range A extends up to about 45 degrees. In another embodiment, the angular range A extends up to about 30 degrees.

Crown 550 is received in coupling member 530 adjacent anchor member 70, and includes at least one seat portion 552 that extends outwardly from coupling member 530 through an aligned one of the windows 548. Locking member 590 is engageable to coupling member 530 to secure plate member 120 against crown 550, as shown in FIG. 32. The downwardly or distally directed securing force supplied by engagement of locking member 590 can also seat crown 550 on the proximal end of anchor member 70 to rigidly engage anchor member 70 in the desired position relative to coupling member 530.

Coupling member 530 includes proximally extending post 532 and lower receiver portion 534 centered about longitudinal axis 521. Post 532 includes a reduced size relative to receiver portion 534 so that post 532 can pass through an opening of the implant while at least a portion of the receiver portion 534 is sized to prevent passage through an opening of the implant. Coupling member 530 includes an upper passage portion 542 extending through post 532 in communication with a receptacle 544 defined in receiver portion 534. Receiver portion 534 includes an inner thread profile 546 adjacent receptacle 544 for threadingly receiving and engaging retaining clip 560 therein.

Retaining clip 560 includes an externally threaded engaging portion 564 and a distal retaining portion 562. A bore 566 extends through engaging portion 564 and retaining portion 562, and receives the threaded shaft of anchor member 70 therethrough. As shown in FIG. 32, bore 566 includes a proximal portion sized to receive a cup portion 554 of crown 550 therein with the proximal end of anchor member 70 in cup portion 554. Distal retaining portion 562 includes a radially inwardly extending flange 568 that extends about and contacts the head of anchor member 70 distally of its greatest outer dimension to retain anchor member 70 in coupling member 530. The threaded engagement between retaining clip 560 and coupling member 530 provides a secure coupling arrangement of anchor member 70 in lower receiver portion 534, while facilitating assembly and disassembly of anchor member 70 with coupling member 530 without deformation or bending of retaining clip 560.

Post 532 can include a circular outer surface with an external thread profile to threadingly engage locking member 590. Post 532 can also be configured with opposite flats along its outer surface as discussed above. Upper passage portion 542 of post 532 defines a proximally opening tool engaging passage 536 with internal surfaces forming a non-circular cross-section configured to engage a tool to facilitate rotating coupling member 530 about longitudinal axis 521. In addition, passage portion 542 can be sized to permit passage of a driving instrument to engage anchor member 70 captured in receiver portion 534 and apply a driving force directly to anchor member 70 through coupling member 530.

Crown 550 includes seat portion 552 positioned proximally of a lower cup portion 554. Seat portion 552 includes a number of arms 553 axially extending therefrom with recesses formed between adjacent ones of the arms 553. Seat portion 552 includes axially extending arms 553 that are sized relative to windows 548 to extend therethrough and project outwardly therefrom so that the implant positioned thereabout will be supported at least in part by crown 550. As shown in FIG. 31, seat portion 552 forms a proximally opening cup shape with a central recessed area 557 and valleys 558 between arms 553. Cup portion 554 includes a semi-spherically shaped body projecting distally from seat portion 552 with a distally facing opening formed at its distal end. Cup portion 554 defines a receptacle 559 having a concavely curved inner surface adapted to receive the shape of the proximal end of anchor member 70 positioned in coupling member 530. A through-hole 556 extends through seat portion 552 and is in communication with receptacle 559, allowing placement of a driving instrument therethrough for engagement with a tool recess in the proximal end of anchor member 70 positioned in cup portion 554.

FIGS. 30-32 show one embodiment of a locking member 590 engageable to post 532 of coupling member 530. Locking member 590 includes a body 592 having a sidewall 596 extending about a threaded through-bore 594. Through-bore 594 is alignable along the longitudinal axis 521 of anchor assembly 520. When locking member 590 is engaged about post 532 and in contact with plate member 120, as shown in FIGS. 30 and 32, further tightening of locking member 590 against plate member 120 causes plate member 120 to seat on any one or combination of the ends of arms 553 of seating portion 552. This in turn forces crown 550 onto the head of anchor member 70. For an anchor member 70 provided with locking ridges, the anchor member 70 can be rigidly coupled to coupling member 530. Multi-axial coupling arrangements are also contemplated as discussed above. Furthermore, locking member 590 can be provided with a configuration that prevents it from loosening or unthreading along post 532, as discussed above with respect to locking member 590. Other embodiments contemplate other forms for locking member 590, including a locking member with break-off portions to ensure proper torque is applied during engagement, or a locking member providing other engagement relationships with post 532, such as a bayonet-lock, interference fit, or fused connection.

Figures 33, 34:
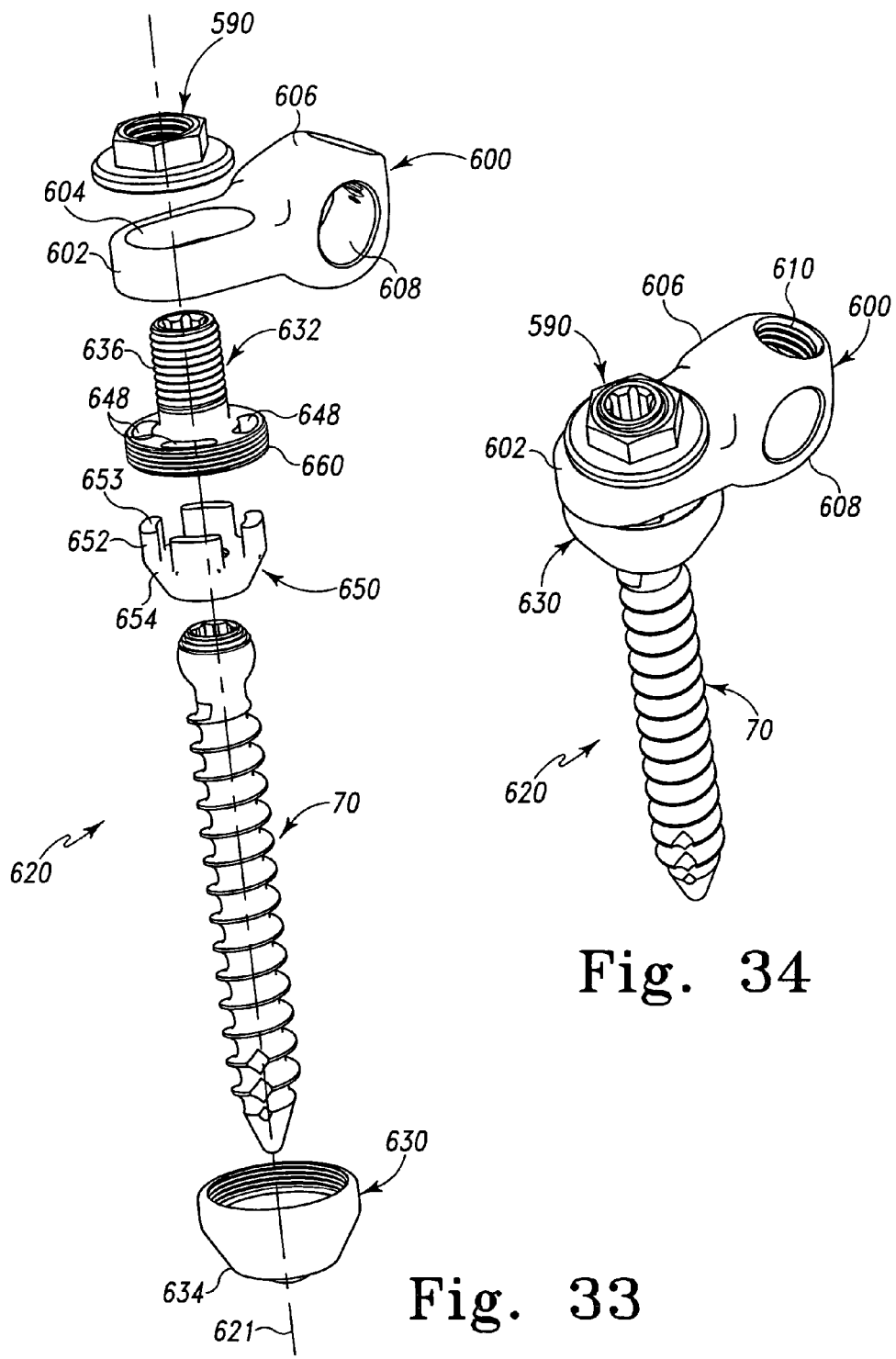
FIG. 33 is an exploded view of another embodiment multi-axial anchor assembly engaged to a plate member.
FIG. 34 is a perspective view of the anchor assembly and plate member of FIG. 33.

FIGS. 33-34 show another embodiment multi-axial anchor assembly 620 provided to secure an implant, such as plate member 600, to one or more vertebrae of the spinal column. In the illustrated embodiment, plate member 600 includes a slotted connector portion 602 defining a slot 604. Other embodiments contemplate non-slotted openings through connector portion 602. Plate member 600 further includes a receiving portion 606 offset from connector portion 602 that defines a receiving passage 608. Receiving passage 608 is transversely oriented to slot 604, and is alignable to receive a rod or other elongate connecting element positionable along the spinal column when connector portion 602 is engaged to a vertebra with an anchor in slot 604. A transverse bore 610 is provided through receiving portion 606 in communication with receiving passage 608. A set screw or other engaging member is positionable in bore 610 to engage the elongate connecting element in passage 608 to secure the connecting element in position relative to the anchor assembly 620. It should be understood that anchor assembly 620 can be employed with any embodiment plate member discussed herein, and that plate member 600 can be employed with any embodiment anchor assembly discussed herein. It is further contemplated that anchor assembly 620 can be employed to secure any type of implant to a bony structure of the spinal column.

Anchor assembly 620 includes anchor member 70 and a locking member 590 such as provided with anchor assembly 520 discussed above, although other embodiment anchors and locking members are contemplated for use in anchor assembly 620. Anchor 70 is top-loaded into and pivotally received in a receiver portion 634 of a coupling member 630. A crown 650 is positionable in receiver portion 634 proximally of the head of the anchor 70. Coupling member 630 further includes a post 632 that is removably engageable to a proximal end of receiver portion 634. In one embodiment, crown 650 in receiver portion 634 extends between anchor member 70 and plate member 600 positioned about post 632. Crown 650 can rigidly engage anchor member 70 in position relative to coupling member 630 and plate member 600 when locking member 590 is secured against plate member 600. Other embodiments contemplate that the angular movement of anchor member 70 is retained even after locking member 590 is secured to plate member 600.

Anchor member 70 can be pivoted relative to plate member 600 when post 632 is positioned through opening 604 of plate member 600. Various angular arrangements for anchor member 70 relative to post 632 are contemplated as discussed herein with respect to the other embodiment anchor assemblies. The angular movement of anchor member 70 relative to post 632 facilitates positioning of anchor member 70 into the vertebrae in a desired orientation while allowing post 632 to be aligned to receive the plate member thereabout.

In one form, post 632 includes a distal engaging portion 660 extending radially outwardly about a distal end of a proximal post portion 636. Engaging portion 660 can be externally threaded to threadingly engage internal threads at the proximal end opening of receiver portion 634. In another form, engaging portion 660 is internally threaded to engage external threads on receiver portion 634. Other coupling arrangements are also contemplated, including friction or interference fits, fusion, adhesives, fasteners, bayonet locks, and snap fits, for example. Engaging portion 660 includes at least one window 648 and crown 650 includes a seat portion 652 formed by at least one axially extending arm 653 projecting through the at least one window 648 for contact with plate member 600 when positioned about post 632. Locking member 590 firmly engages plate member 600 against one or more of the arms 653 of crown 650 when locking member 590 is positioned against plate member 600.

In the illustrated embodiment, engaging portion 660 includes four windows 648 spaced circumferentially thereabout that are also elongated circumferentially. Crown 650 includes four arms 653 defining seat portions 652 extending axially through respective ones of the four windows 648. Other embodiments contemplate an arrangement with two arms and windows, three arms and windows, or more than four arms and windows. It is further contemplated that the same number of arms and windows need not be provided for a particular anchor assembly. Crown 650 can be engaged with anchor member 70 and configured in any of the various manners discussed above with respect to crown 550.

Crown 650 is received in coupling member 630 adjacent anchor member 70, and includes at least one seat portion 652 that extends outwardly from engaging portion 660 through a respective one of the windows 648. Locking member 590 is engageable to post 632 to secure plate member 600 against crown 650, as shown in FIG. 34. The downwardly or distally directed securing force supplied by engagement of locking member 590 can also seat crown 650 on the proximal end of anchor member 70 to rigidly engage anchor member 70 in the desired position relative to coupling member 630 and post 632. In one embodiment, crown 650 includes a lower cup portion 654 having an outer surface profile that conforms to the inner surface profile of receiver portion 634 to permit pivotal movement of the head of anchor member 70 in receiver portion 634 at least before locking member 590 is engaged against the implant.

Coupling member 630 includes lower receiver portion 634 centered about longitudinal axis 621 with engaging portion 660 engageable at a proximal end of receiver portion 634 and post portion 636 extending proximally therefrom along axis 621. Post portion 636 includes a reduced size relative to receiver portion 634 so that post portion 636 can pass through an opening of the plate member while at least a portion of engaging portion 660 and receiver portion 634 are sized to prevent passage through opening 604 of plate member 600. Post 632 includes a circular outer surface with an external thread profile to threadingly engage locking member 590. Post 632 can also be configured with opposite flats along its outer surface as discussed above.

Post 632 can also define a proximally opening tool engaging passage with internal surfaces forming a non-circular cross-section configured to engage a tool to facilitate rotating post portion 636 and engaging portion 660 about longitudinal axis 621. The passage can be sized to permit passage of a driving instrument to engage anchor member 70 captured in receiver portion 634 and apply a driving force directly to anchor member 70 through post 632.

Figures 35, 36:
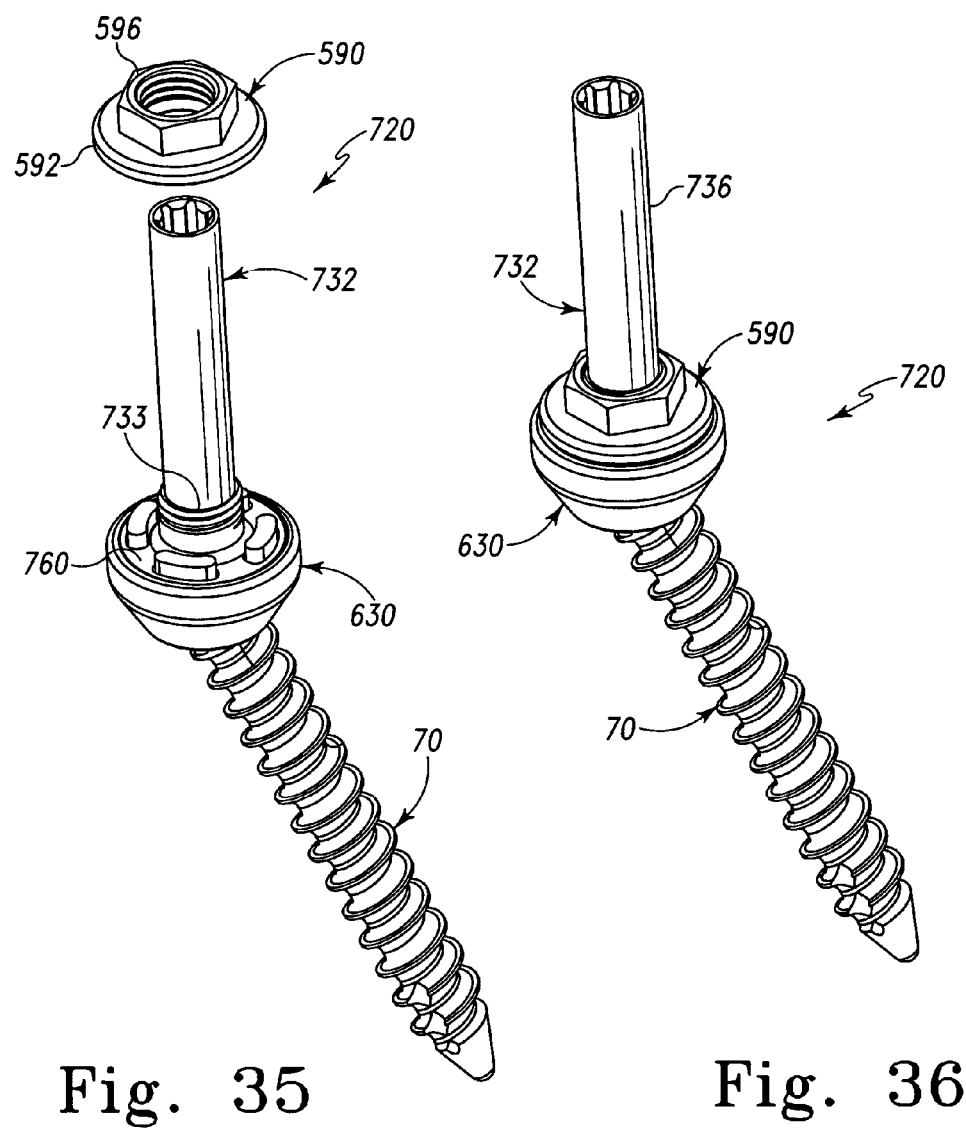
FIG. 35 is an exploded view of another embodiment multi-axial anchor assembly engaged to a plate member.
FIG. 36 is a perspective view of the anchor assembly and plate member of FIG. 35.

Referring now to FIGS. 35 and 36, there is shown another embodiment anchor assembly 720 that is similar to anchor assembly 620 discussed above. Anchor assembly 720 includes anchor member 70 pivotally received in coupling member 630 and crown 650 positioned adjacent the head of anchor member 70 and extending axially through axially extending windows of engaging portion 760. Post 732 is similar to post 632, but includes a post portion 736 having a smooth non-threaded outer surface extending along a substantial portion of the length thereof. In one form, the smooth portion 736 has a length sufficient to receive a connector that engages another spinal implant, such as a rod or tether. The distal end of post 732 includes a thread profile 733 to threadingly engage locking member 590.

Locking member 590 is engageable along thread profile 733 to position the distal end of body 592 in contact with the axially extending arms of crown 650 to secure anchor member 70 in position as discussed above with respect to anchor assembly 620. The connector or other implant can be engaged to post 732 proximally of locking member 590. The connector can be secured in position by engaging post 732 with a set screw, clamping arrangement, friction fit or other suitable coupling arrangement. Other embodiments contemplate a second locking member can be engaged to post 732 proximally of the connector to clamp the connector between locking members.

In one technique employing the anchor assemblies discussed herein, the plate member is sized to contact neighboring vertebrae, and includes at least one opening adjacent those vertebrae so that the coupling member of the anchor assembly can be placed through the at least one opening when the anchor member of the anchor assembly is engaged to the underlying bony structure. In another embodiment, the anchor assemblies can be provisionally captured on the plate member with a locking member prior to engagement with the bony structure. The plate members may also be sized and configured to extend across more than two vertebrae for multi-level stabilization procedures, or configured for engagement with a single vertebra with a receiving member for receiving an elongate connecting element, such as a rod or plate, positionable along two or more vertebrae.

The plate members can be pre-bent or bent during surgery to include a curvature, for example, to replicate or conform to a natural or desired spinal curvature. It will be understood that any curvature appropriate for one or more segments of the spine (whether cervical, thoracic, lumbar or sacral) could be incorporated into plate member. Such curvatures can include entirely convex, entirely concave, entirely straight (i.e. essentially planar), and combinations thereof. It is further contemplated that the plate can be engaged to the anterior, oblique, lateral, or posterior bony portions of one or more vertebrae.

The illustrated embodiments of the plate members herein do not show a retaining member on or engageable to the plate member to prevent or resist backout of the locking member. However, the plate members may be provided with one or more retaining elements to prevent backout of any portion of the anchor assembly relative to the plate member. The retaining elements may be any one or combination of a set screw, set screw and washer, spring-loaded member, sliding washer or other similar device attached to, captured on or integrally formed with the plate member.

For ease of use, a kit containing one or more of the parts of any one or combination of the implant assemblies may be provided. For example, a kit may include several embodiments of plate members in several different lengths, sizes, slot configurations, and/or curvatures. Lengths or sizes appropriate for cervical, thoracic, lumbar and/or sacral implantation may be included. One or more sets of multi-axial and uni-axial anchor assemblies can be provided with various anchor member sizes and coupling members adapted for attachment to one or more of the cervical, thoracic, lumbar and sacral regions of the spine may also be provided in such a kit. The kit may further include multiple multi-axial anchor assemblies that include those configured to provide rigid stabilization and dynamic stabilization of the spinal column when engaged to the plate member.

A method of using one or more multi-axial anchor assemblies discussed herein will now be described. The anchor assemblies can be employed in open surgical procedures where skin and tissue is retracted, and in minimally invasive surgical procedures where the anchor assembly and/or plate members are positioned in the patient with one or more minimally invasive access approaches formed by micro-incisions, retractors, sleeves, and expanding sleeves.

In one procedure, a surgeon will make an incision into the patient at a place relatively proximate to the vertebrae or other bone(s) to which the implant is to be attached. After the appropriate access to the surgical site is obtained, a portion of the inferior vertebra to be instrumented (e.g. the pedicle) is prepared in a standard manner. For example, an awl or drill may be used to prepare a hole, which is then probed for depth and tapped if appropriate for the anchor member. One of the anchor members is then inserted into the hole in the inferior vertebra with a coupling member engaged thereto. Access to a portion of the superior vertebra (e.g. the pedicle) to be instrumented is then obtained, either via the previous incision or via a separate incision. The point on the superior vertebra at which the implant is to be attached is identified, and the vertebra is prepared as described above. Another anchor assembly is engaged to the superior vertebra, and at least one of the anchor assemblies is a multi-axial anchor assembly. The at least one multi-axial anchor assembly can be configured to provide either rigid or dynamic stabilization when engaged to the plate member, as discussed above. The process is repeated for any one or more vertebrae between the superior and inferior vertebrae if desired.

A plate member is then inserted directly through the incision or through an access tube or retractor to the anchor assemblies. The post of each of the at least one multi-axial anchor assembly coupling members is positioned through or bottom-loaded through an opening of the plate member. The orientation and axial location of the coupling member relative to the anchor member and the plate member can be adjusted. When the plate member and anchor assemblies are in the desired position relative to one another and the spinal column, the locking member can be advanced to secure the respective anchor assembly and plate member relative to one another in the desired position. Prior to finally securing the plate member to the anchor assemblies, the vertebra can be compressed or distracted and maintained in this position with the secured plate member. It is further contemplated that one or more disc spaces or posterior elements between vertebrae can be fused with any one or combination of bone graft, bone material, and implants. For anchor assemblies employing a coupling member with an extended post, the extension portion of the post can be removed after securement of the plate to the anchor assembly.

It will further be appreciated that the embodiments described above should be made of materials suitable for implantation within the human or other body, and may consist of inert metals like titanium or stainless steel. Other sturdy materials such as certain ceramics or plastics may also be considered. Bio-resorbable materials, such as polylactic acid compounds, may be used along with or as a part of the parts described above. In one embodiment, a non-metal plate is employed with the anchor assemblies. The engagement of the anchor assemblies to the non-rigid plate includes at least some flexibility for flexible spinal stabilization, allowing at least limited motion of the instrumented vertebral level. Spinal motion can be enhanced by providing the anchor assembly in a form that dynamically engages the plate member to the spinal column, as discussed above.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An anchor assembly, comprising:
    an anchor member including a proximal end and a distal portion extending from said proximal end for engagement with a bone member;
    a coupling member pivotally coupled to said proximal end of said anchor member, said coupling member extending along a longitudinal axis and including a lower receiver portion defining an interior receptacle extending about said longitudinal axis for receiving said proximal end of said anchor member with said distal portion of said anchor member extending distally from said lower receiver portion, said coupling member further including a post extending proximally from said receiver portion along said longitudinal axis away from said proximal end of said anchor member, said coupling member defining at least one axially opening window in communication with an exterior of said coupling member;
    a member positioned around said post proximally of said anchor member so that said post extends through said member; and
    a crown positioned in said receptacle of said coupling member adjacent said proximal end of said anchor member, said crown including a seating portion extending proximally from said anchor member along said longitudinal axis, wherein said seating portion of said crown includes at least three axially extending arms circumferentially distributed about said crown, and said at least one window of said coupling member includes at least three axially extending windows circumferentially distributed about said coupling member that extend through said coupling member between said interior receptacle and said exterior, each of said number of arms extend proximally from within said receptacle and through a respective one of said number of windows and contact said member positioned around said post with said post extending through said member.

2. The assembly of claim 1, wherein said post includes an internal passage extending along said longitudinal axis in communication with said receptacle of said receiver portion.

3. The assembly of claim 1, wherein said anchor member includes a threaded shaft along said distal portion and enlarged head at said proximal end.

4. The assembly of claim 3, further comprising a retaining clip positioned about said neck portion and extending between said coupling member and said head, said retaining clip including a threaded portion threadingly engaging said coupling member about a distally oriented opening of said receptacle, said retaining clip including a radially inwardly extending flange extending about said head of said anchor member sized to prevent passage of said head therethrough to retain said anchor member in said coupling member.

5. The assembly of claim 3, wherein said head includes a plurality of ridges extending thereabout oriented toward said crown.

6. The assembly of claim 5, wherein said plurality of ridges engage said crown when said member is secured against said seating portion, said engagement between said ridges and said crown preventing said anchor member from pivoting relative to said coupling member.

7. The assembly of claim 1, wherein said post is smooth along a substantial portion of a length thereof.

8. The assembly of claim 7, wherein said post includes a thread profile adjacent a distal end thereof, and said member is a locking member threadingly engageable with said thread profile in contact with said seating portion.

9. The assembly of claim 1, wherein said crown includes a distally opening cup portion extending from said seat portion, said cup portion including a receptacle for receiving said proximal end said anchor member therein.

10. The assembly of claim 1, wherein said post includes a circular cross-section and external threads thereabout for threadingly engaging said member.

11. The assembly of claim 1, wherein said post includes a distal engaging portion extending radially about a distal end of a threaded post portion, said engaging portion being threadingly engageable with a proximal end opening of said lower receiver portion.

12. The assembly of claim 11, wherein said at least one window extends through said engaging portion of said post.

13. An anchor assembly, comprising:
    an anchor member including a proximal end and a distal portion extending from said proximal end for engagement with a bone member;
    a coupling member pivotally coupled to said proximal end of said anchor, said coupling member extending along a longitudinal axis and including a lower receiver portion defining an interior receptacle extending about said longitudinal axis for receiving said proximal end of said anchor member with said distal portion extending distally from said lower receiver portion, said coupling member including a post extending proximally from said receiver portion along said longitudinal axis away from said proximal end of said anchor member, said coupling member defining at least one axially opening window in communication with an exterior of said coupling member;
    a member positioned proximally of said proximal end of said anchor member with said post extending through said member; and
    a crown positioned in said receptacle of said coupling member adjacent said proximal end of said anchor member, said crown including a seating portion extending proximally from said anchor member along said longitudinal axis, wherein said seating portion of said crown includes at least three axially extending arms circumferentially distributed about said crown, and said at least one window of said coupling member includes at least three axially extending windows circumferentially distributed about said coupling member that extend through said coupling member between said interior receptacle and said exterior, each of said number of arms extend proximally from within said receptacle and through a respective one of said number of windows to said exterior where said arms contact said member with said post extending through said member.

14. The assembly of claim 13, wherein said post includes an internal passage extending along said longitudinal axis in communication with said receptacle of said receiver portion.

15. The assembly of claim 13, wherein said post is smooth along a substantial portion of a length thereof.

16. The assembly of claim 15, wherein said post includes a thread profile adjacent a distal end thereof, and said member is a locking member threadingly engageable with said thread profile in contact with said seating portion.

17. The assembly of claim 13, wherein said crown includes a distally opening cup portion extending from said seat portion, said cup portion including a receptacle for receiving said proximal end said anchor member therein.

18. The assembly of claim 13, wherein said post includes a distal engaging portion extending radially about a distal end of a threaded post portion, said engaging portion being threadingly engageable with a proximal end opening of said lower receiver portion.

19. The assembly of claim 18, wherein said at least one window extends through said engaging portion of said post.

20. An anchor assembly, comprising:
an anchor member including a proximal end and a distal portion extending from said proximal end for engagement with a bone member;
a coupling member pivotally coupled to said proximal end of said anchor, said coupling member including a lower receiver portion defining an interior receptacle extending about said axis for receiving said proximal end of said anchor member and a post extending from said receiver portion along a longitudinal axis away from said proximal end of said anchor member, said coupling member defining at least three axially opening windows proximally of said proximal end of said anchor member that extend through said coupling member from said interior receptacle to an exterior of said coupling member,
a member positioned proximally of said proximal end of said anchor member with said post extending through said member; and
a crown positioned in said receptacle of said coupling member adjacent said proximal end of said anchor member, said crown including a distal portion receiving said anchor member in said receptacle of said coupling member and said crown also includes at least three arms extending proximally along said longitudinal axis and proximally from said proximal end of said anchor member in said receptacle of said coupling member to locate said at least three arms through said at least three windows and to position said member in contact with said at least three arms with said post extending through said member.

21. An anchor assembly, comprising:
an anchor member including a proximal end and a distal portion extending from said proximal end for engagement with a bone member;
a coupling member pivotally coupled to said proximal end of said anchor member, said coupling member extending along a longitudinal axis and including a lower receiver portion defining an interior receptacle extending about said longitudinal axis for receiving said proximal end of said anchor member and a post extending from said receiver portion along said longitudinal axis away from said proximal end, wherein said post includes a distal engaging portion extending radially outwardly about a distal end of a threaded post portion, said engaging portion being threadingly engaged to threads extending around a proximal end opening of said lower receiver portion and said coupling member defines at least one window around said post that extends through said engaging portion between said interior receptacle and a proximal side of said engaging portion;
a member positioned around said post so that said post extends through said member; and
a crown positioned in said receptacle of said coupling member adjacent said proximal end of said anchor member, said crown including a seating portion extending along said longitudinal axis and in communication with said at least one window for positioning said seating portion in contact with said member with said member positioned around said post with said post extending through said member.

22. The assembly of claim 21, wherein said at least one window extends through said distal engaging portion of said post.

* * * * *